United States Patent
Kisner et al.

(10) Patent No.: US 10,354,412 B2
(45) Date of Patent: Jul. 16, 2019

(54) RECEPTACLE FOR DETECTION OF TARGETED SUBSTANCES

(71) Applicant: DETECTACHEM, INC., Stafford, TX (US)

(72) Inventors: Travis Kisner, Sugar Land, TX (US); Derek Roosken, Houston, TX (US); Aaron Sanders, Meadows Place, TX (US)

(73) Assignee: DETECTACHEM, INC., Stafford, TX (US)

( * ) Notice: Subject to any disclaimer, the term of this patent is extended or adjusted under 35 U.S.C. 154(b) by 311 days.

(21) Appl. No.: 15/156,766

(22) Filed: May 17, 2016

(65) Prior Publication Data

US 2017/0153185 A1    Jun. 1, 2017

Related U.S. Application Data

(60) Provisional application No. 62/261,098, filed on Nov. 30, 2015.

(51) Int. Cl.
*G01N 31/22* (2006.01)
*G06T 7/90* (2017.01)
(Continued)

(52) U.S. Cl.
CPC ............. *G06T 7/90* (2017.01); *G01N 21/274* (2013.01); *G01N 21/78* (2013.01); *G06K 9/2063* (2013.01);
(Continued)

(58) Field of Classification Search
CPC .. G06T 7/90; G06T 7/80; G06T 5/001; G06T 2207/10024; G01N 21/274; G01N 21/78;
(Continued)

(56) References Cited

U.S. PATENT DOCUMENTS 6,524,530 B1 * 2/2003 Igarashi ................ B01L 3/5029
                                                        422/411
7,344,081 B2 * 3/2008 Tseng .................. G01N 21/8483
                                                        235/375
(Continued)

FOREIGN PATENT DOCUMENTS

| WO | 2014/081460 | 5/2014 |
| WO | 2014/113770 | 7/2014 |
| WO | 2014/145663 | 9/2014 |

OTHER PUBLICATIONS

U.S. Appl. No. 29/564,988 to Travis Kisner et al., filed May 17, 2016.
(Continued)

*Primary Examiner* — Dennis White
(74) *Attorney, Agent, or Firm* — Greenblum & Bernstein, P.L.C.

(57) ABSTRACT

A receptacle for detecting a targeted substance is provided and may include at least one chamber configured to accommodate a reagent and a test swab. A first opening may be provided at a first end of the receptacle and a testing area may be provided at a second end of the receptacle. The receptacle may further include an image, readable by an image sensor, that is positioned a predetermined distance from the testing area and configured to facilitate alignment of the image sensor with the testing area for a colorimetric analysis of the targeted substance.

11 Claims, 26 Drawing Sheets

(51) Int. Cl.
*G06T 5/00* (2006.01)
*G01N 21/78* (2006.01)
*G06K 9/32* (2006.01)
*G06K 9/20* (2006.01)
*G06K 9/46* (2006.01)
*G06T 7/80* (2017.01)
*G01N 21/27* (2006.01)

(52) U.S. Cl.
CPC ......... *G06K 9/3216* (2013.01); *G06K 9/4652* (2013.01); *G06T 5/001* (2013.01); *G06T 7/80* (2017.01); *G06T 2207/10024* (2013.01)

(58) Field of Classification Search
CPC ... G06K 9/4652; G06K 9/2063; G06K 9/3216
See application file for complete search history.

(56) References Cited

U.S. PATENT DOCUMENTS

| | | | |
|---|---|---|---|
| 8,744,180 B2 | 6/2014 | Atsmon et al. | |
| 8,750,613 B2 | 6/2014 | Lee | |
| 8,872,923 B2 | 10/2014 | Gottwals et al. | |
| 8,885,936 B2 | 11/2014 | Webb et al. | |
| 8,948,508 B2 | 2/2015 | Zheng et al. | |
| 8,980,641 B2 | 3/2015 | Clift et al. | |
| D727,762 S | 4/2015 | Kisner et al. | |
| 2004/0151624 A1 | 8/2004 | Erdman, Jr. et al. | |
| 2009/0325300 A1 | 12/2009 | Clift et al. | |
| 2012/0189509 A1* | 7/2012 | Hsiao | G01N 21/274 422/400 |
| 2012/0288195 A1 | 11/2012 | Lings et al. | |
| 2013/0267032 A1 | 10/2013 | Tsai et al. | |
| 2014/0314625 A1 | 10/2014 | Clift et al. | |
| 2015/0015598 A1 | 1/2015 | Lichman | |
| 2015/0055134 A1 | 2/2015 | Papautsky et al. | |
| 2015/0290638 A1 | 10/2015 | Kisner et al. | |
| 2015/0304555 A1 | 10/2015 | Ehrenkranz | |
| 2016/0041134 A1 | 2/2016 | Kisner | |
| 2016/0048739 A1* | 2/2016 | Burg | H05K 999/99 382/128 |

OTHER PUBLICATIONS

U.S. Appl. No. 15/156,803 to Travis Kisner et al., filed May 17, 2016.

* cited by examiner

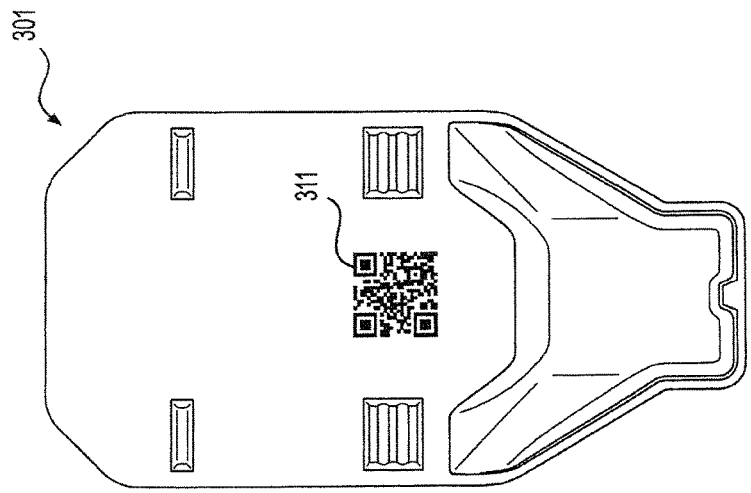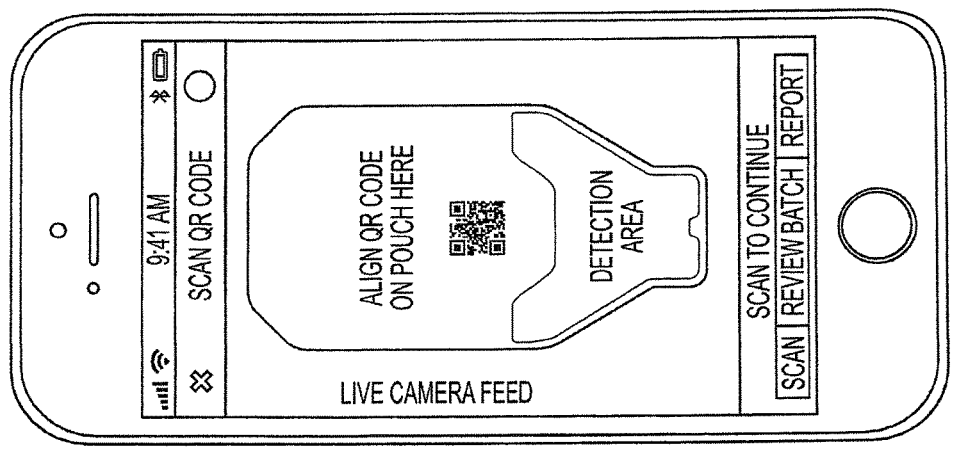
FIG. 15A

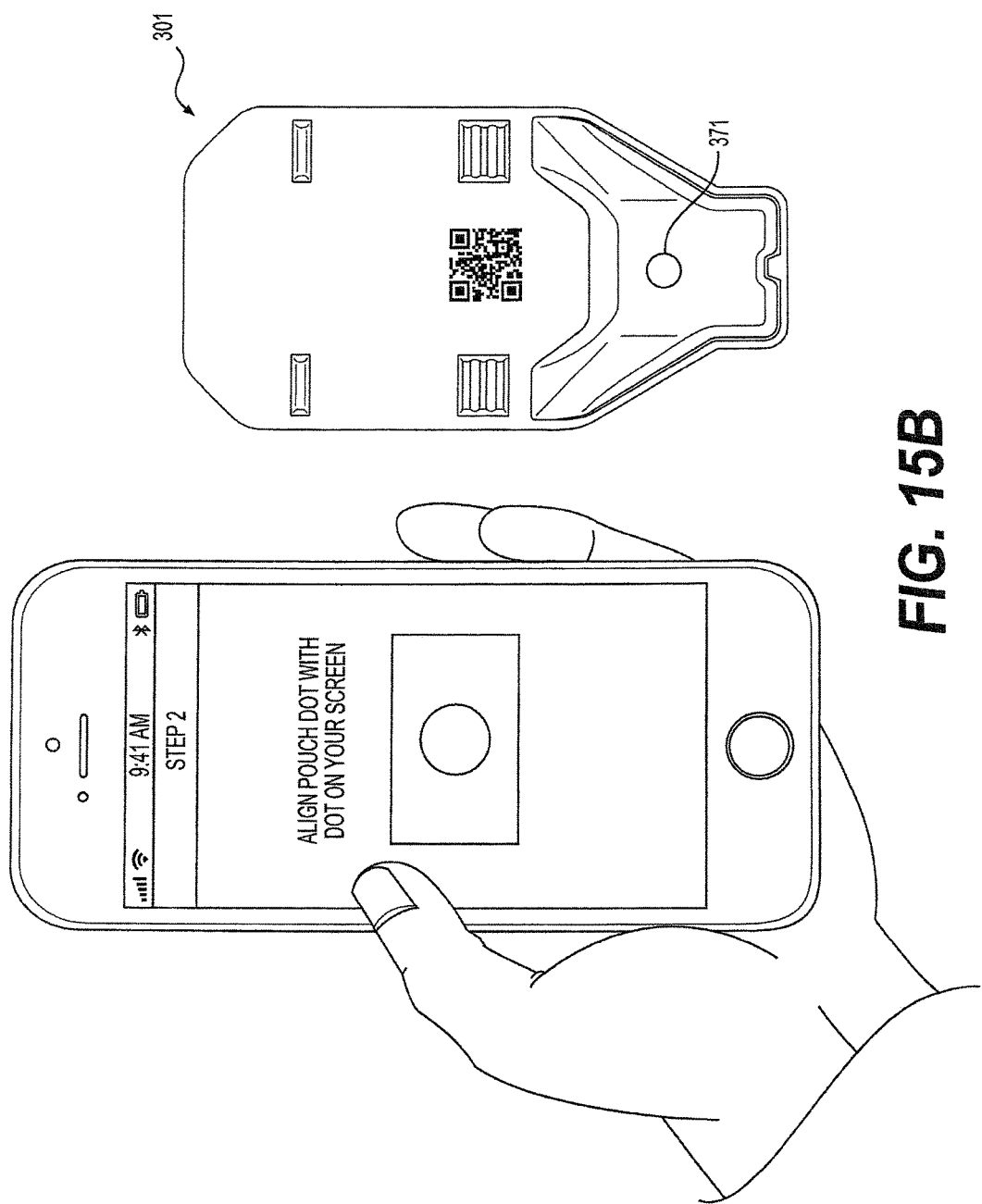

RECEPTACLE FOR DETECTION OF TARGETED SUBSTANCES

CROSS-REFERENCE TO RELATED APPLICATION

This application claims the benefit of U.S. Provisional Patent Application No. 62/261,098 filed on Nov. 30, 2015, the disclosure of which, including specification, drawings, and claim, is expressly incorporated herein by reference in its entirety.

BACKGROUND

1. Field of the Disclosure

The present disclosure relates to the field of detection of targeted substances, e.g., chemicals, drugs, explosives, and biological agents. More particularly, the present disclosure relates to a receptacle for the collection of the targeted substances and the performance of an analysis to determine the presence of the targeted substance. The detection of the substance can be performed by a computing device, e.g., a portable computing device for detection, data collection, and communications.

2. Background Information

Various groups, including those in law enforcement, military, private security, agriculture, medical profession, and parents may have a need for a method of detecting the presence of substances.

BRIEF DESCRIPTION OF THE DRAWINGS

FIG. 15A shows exemplary aligning indicia displayed on the computing device by the application with indicia such as an identification code or other indicia on the receptacle, according to an aspect of the present disclosure;

FIG. 15B shows exemplary aligning indicia displayed on the computing device by the application with indicia such as an identification code or other indicia on the receptacle, according to an aspect of the present disclosure;

DETAILED DESCRIPTION

Figure 1:
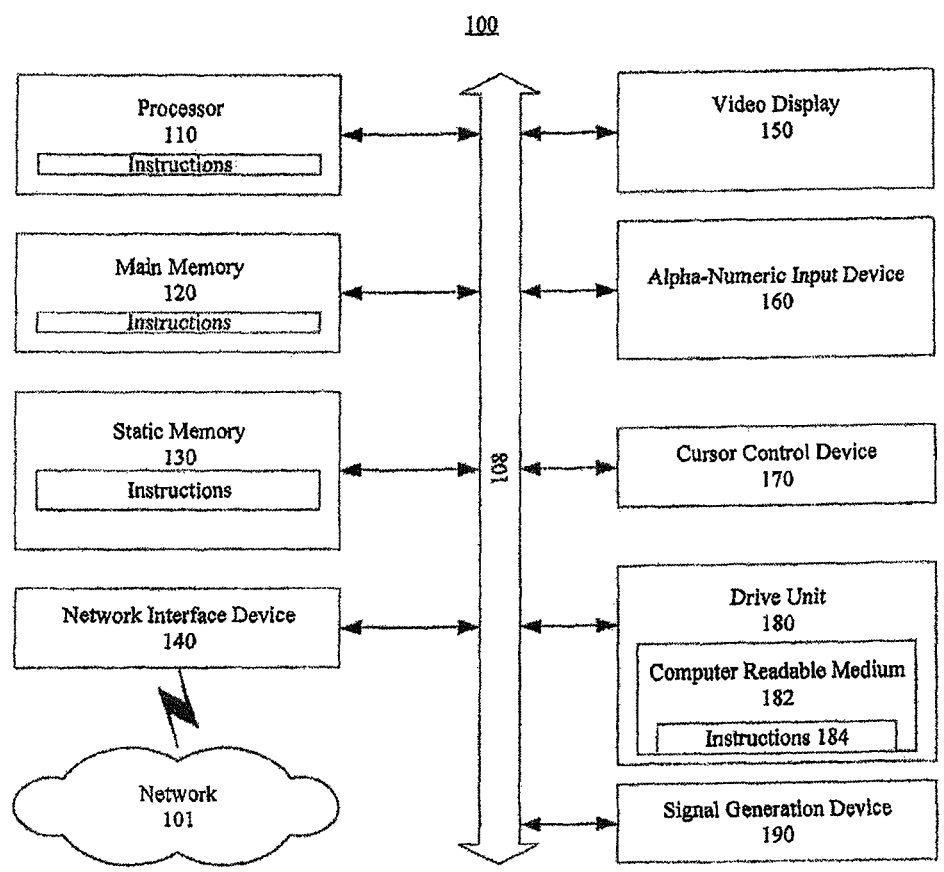
FIG. 1 shows an exemplary general computer system that includes a set of instructions for the apparatus and method for detection of substances, according to an aspect of the present disclosure.

In view of the foregoing, the present disclosure, through one or more of its various aspects, embodiments and/or specific features or sub-components, is thus intended to bring out one or more of the advantages as specifically noted below.

Methods described herein are illustrative examples, and as such are not intended to require or imply that any particular process of any embodiment be performed in the order presented. Words such as "thereafter," "then," "next," etc. are not intended to limit the order of the processes, and these words are instead used to guide the reader through the description of the methods. Further, any reference to claim elements in the singular, for example, using the articles "a," "an" or "the", is not to be construed as limiting the element to the singular.

The apparatus and method provides for the automated colorimetric detection of targeted substances with reporting and evidence collection tools. It makes it easy for users such as law enforcement to accurately detect substances of interest while removing the hassle of reporting and paperwork. The reporting functionality allows a user to transmit results over a communications network as desired.

The present disclosure pertains to a colorimetric system for detecting a substance. The colorimetric system includes a receptacle or pouch within which one or more ampoules are adapted to release one or more chemicals (e.g., reagents) to an area defining a test location. The test location may include a swab to which the substance is applied. The one or more chemicals are released to flow, by gravity, to at least one test area. In systems where multiple ampoules are utilized, sequencing of the chemicals from those ampoules can be done to achieve sequential chemical flows, resulting in multiple chemical reactions facilitating more complex colorimetric detection.

Embodiments of the present disclosure can be used to detect substances that require one or more chemical reactions to perform a colorimetric reaction. Embodiments may include using a chemical reaction to modify the molecular structure of a substance before a subsequent defined chemical reaction can be executed to provide for the colorimetric reaction process to identify the substance in the colorimetric reaction.

Automated colorimetric detection is the use of a known computing device with known detection algorithms and optics to give a determination of the presence of a targeted substance without the interpretation of the human vision or sight. Manual colorimetric detection is different from automated in that it requires human color recognition through vision or eyesight for the determination of a targeted substance and result determination.

Essentially, a sample of the unknown trace is collected on the test area of the swab or inserted into the testing area of the receptacle. A chemical reaction with the unknown substance is initiated using liquid reagents and dissolve compounds contained in at least one ampoule contained in the receptacle. A reaction is initiated after inserting the swab, or bulk substance, in the receptacle and rupturing the ampoules, thus establishing fluid communication between the reagents and the unknown substance. The fluid communication may be established via specific paths like channels or grooves defined in the pouch or with wicks via capillary action by virtue of a snug fit of the components of the receptacle, as will be explained in further detail herein. Further, chemicals from the ampoules may be released to react in specific regions of the swab or receptacle or the regions may be temporally separated for chemical reactions.

In one embodiment, the application discussed herein uses a smartphone camera to detect the color of a chemical reaction, and compares the color against known wavelengths of colors, to identify a targeted substance.

FIG. 1 is an illustrative embodiment of a general computer system, on which a method of detection of trace and bulk substances can be implemented, and which is shown and is designated 100. The computer system 100 can include a set of instructions that can be executed to cause the computer system 100 to perform any one or more of the methods or computer based functions disclosed herein. The computer system 100 may operate as a standalone device or may be connected, for example, using a network 101, to other computer systems or peripheral devices.

In a networked deployment, the computer system 100 may operate in the capacity of a server or as a client user computer in a server-client user network environment, or as a peer computer system in a peer-to-peer (or distributed) network environment. The computer system 100 can also be implemented as or incorporated into various devices, such as a stationary computer, a mobile computer, a personal computer (PC), a laptop computer, a tablet computer, a wireless smart phone, a set-top box (STB), a personal digital assistant (PDA), a global positioning satellite (GPS) device, a computing device, a control system, a camera, a web appliance, a network router, switch or bridge, or any other machine capable of executing a set of instructions (sequential or otherwise) that specify actions to be taken by that machine. The computer system 100 can be incorporated as, or in, a particular device that in turn is in an integrated system that includes additional devices. In a particular embodiment, the computer system 100 can be implemented using electronic devices that provide voice, video or data communication. Further, while a single computer system 100 is illustrated, the term "system" shall also be taken to include any collection of systems or sub-systems that individually or jointly execute a set, or multiple sets, of instructions to perform one or more computer functions. The computer system 100 may include a computing device including a camera (e.g., code reader, image reader, and/or scanner, etc.) having an optical system configured to capture images. The computer system 100 may include a smart phone or other computing device having communications software for transmitting and receiving communications over a network. The camera of the computing device may be internal or external to the computer system 100. Of course, the computer system 100 may be powered by alternating current or direct current and may include a battery configured to power the apparatus. The computer system 100 may be portable.

As illustrated in FIG. 1, the computer system 100 includes a processor 110. A processor for a computer system 100 is tangible and non-transitory. As used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. A processor is an article of manufacture and/or a machine component. A processor for a computer system 100 is configured to execute software instructions in order to perform functions as described in the various embodiments herein. A processor for a computer system 100 may be a general purpose processor or may be part of an application specific integrated circuit (ASIC). A processor for a computer system 100 may also be a microprocessor, a microcomputer, a processor chip, a controller, a microcontroller, a digital signal processor (DSP), a state machine, or a programmable logic device. A processor for a computer system 100 may also be a logical circuit, including a programmable gate array (PGA) such as a field programmable gate array (FPGA), or another type of circuit that includes discrete gate and/or transistor logic. A processor for a computer system 100 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 100 includes a main memory 120 and a static memory 130 that can communicate with each other via a bus 108. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 100 may further include a video display unit 150, such as a liquid crystal display (LCD), an organic light emitting diode (OLED), a flat panel display, a solid state display, or a cathode ray tube (CRT). Additionally, the computer system 100 may include an input device 160, such as a keyboard/virtual keyboard or touch-sensitive input screen or speech input with speech recognition, and a cursor control device 170, such as a mouse or touch-sensitive input screen or pad. The computer system 100 can also include a disk drive unit 180, a signal generation device 190, such as a speaker or remote control, and a network interface device 140.

In a particular embodiment, as depicted in FIG. 1, the disk drive unit 180 may include a computer-readable medium 182 in which one or more sets of instructions 184, e.g. software, can be embedded. Sets of instructions 184 can be read from the computer-readable medium 182. Further, the instructions 184, when executed by a processor, can be used to perform one or more of the methods and processes as described herein. In a particular embodiment, the instructions 184 may reside completely, or at least partially, within the main memory 120, the static memory 130, and/or within the processor 110 during execution by the computer system 100.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

One aspect of the testing application is designed for a computing device such as smartphone; however, any computing device may be employed, including any client device or user device. The testing application is configured to detect various substances with examples being explosives, including both military and commercial grade, drugs, bio-hazards, homemade explosives (HMEs) and toxins. The application analyzes and works with a receptacle and an optional swab to sample both trace and bulk amounts of substances of interest. Colorimetric reactions are analyzed with the application operating on a computing device. Results are displayed on the application with other test information and logged for later viewing. The application includes report building tools that allow the user to collect pictures, incorporate notes, add a location, and more to a test result. For example, the information and pictures are packaged together and built into a single report that can be exported in various ways. The application also includes live help videos, detailed drug and explosive definition libraries, in-application receptacle purchasing, activity logging, etc.

The application uses the camera of the computing device (e.g., smartphone) (or other optical camera, or any other device such as a photosensor, visible light sensor, spectrometer, etc.) to analyze the swab inside of the receptacle and immediately determine if the targeted substance is present. The application reports the result along with other test data and displays it clearly for the user. The user then has the option to take the result and create a report by adding more data such as pictures, notes, location, etc. The data is packaged together in a report and can be exported in a variety of ways.

Figure 2:
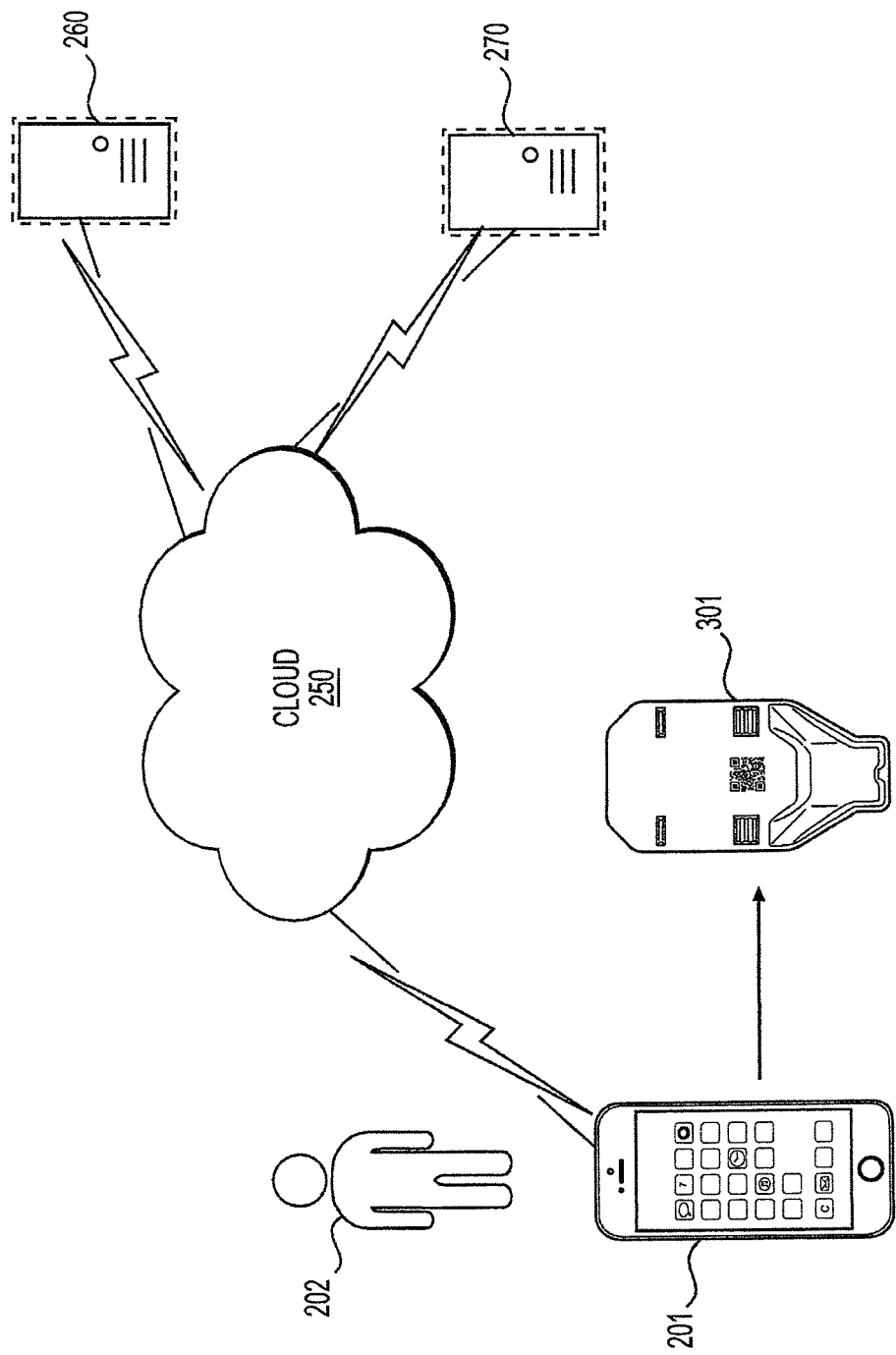
FIG. 2 is an exemplary embodiment of an implementation of an apparatus and method associated with the detection of trace and bulk substances, according to an aspect of the present disclosure.

FIG. 2 is an exemplary embodiment of an implementation of an apparatus and method associated with the detection of trace and bulk substances, according to an aspect of the present disclosure. The computing device 201 is equipped with an optical imaging system, having an image sensor, such as a camera that a user 202 of the computing device 201 can use to capture an image of a chemical reaction test performed within a receptacle 301. After the user 202 captures the image with the camera, the computing device 201 is configured to initiate a colorimetric test via the application on the computing device 201. The colorimetric test may be performed via an application on the computing device 201 or the computing device 201 may transmit the image data over a network to a network node having the requisite combination of hardware and software to complete the colorimetric test and return the test to the computing device 201.

In one embodiment, the computing device 201 may be configured to communicate with a network such as a cloud 250 via one or more appropriate networks. For example, the computing device 201 may transmit data related to an image obtained via the camera of the computing device 201 so that the colorimetric analysis, or any other function associated with testing or reporting, may be performed by the cloud 250. In this regard, the cloud 250 is a computing system including a combination of hardware and software configured to receive requests from the computing device 201 and return responses to the computing device 201. For example, the cloud 250 may be a public cloud(s), private cloud(s), and/or combination of public or private clouds. In addition to or instead of hardware and software, virtual hardware configured to emulate software may be employed. Thus, the colorimetric analysis may be performed on the computing device 201 and/or at the cloud 250. Additionally, the cloud 250 may communicate with one or more external servers or service providers 260, 270 capable of providing the colorimetric analysis and reporting the results back through the cloud 250 to the computing device 201 for review by the user 202. If the colorimetric test is performed locally on the computing device 201, then transmitting the image data to a remote location for testing is not required.

In an alternative embodiment, the computing device 201, cloud 250, and/or service providers 260, 270 may be in communication with a payment system that is configured to generate payment requests and accept payment for conducting the colorimetric tests discussed herein.

Figure 3:
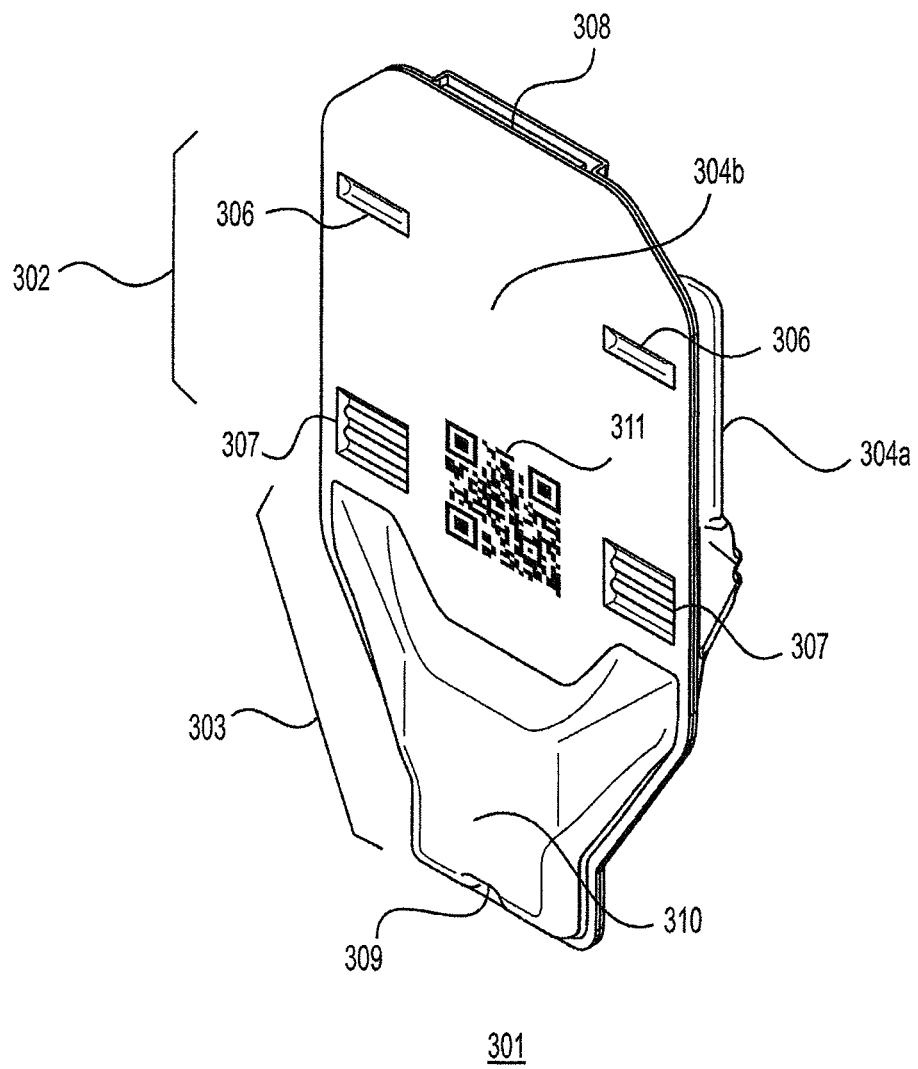
FIG. 3 is an exemplary right side perspective view of a receptacle, according to an aspect of the present disclosure.

FIG. 3 is an exemplary right side perspective view of a receptacle, according to an aspect of the present disclosure. The receptacle 301, also referred to herein as a pouch or a container, includes a main body 302, a neck portion 303 extending from the main body 302, a base 304a and a cover 304b sealed to and extending along peripheral upper side edges of the base 304a side of the main body 302 and the neck portion 303. In one embodiment, the main body 302 houses an upper first chamber and the neck portion 303 houses a lower second chamber. The neck portion 303 is at least partially defined by outwardly extending tapered walls of both the base 304a and the cover 304b projecting from a distal end of the main body 302 such that the neck portion 303 is generally Y-shaped.

Advantageously, the Y-shaped neck portion 303 defines a transition region between the distal end of the main body 302 and the neck portion 303 in order to promote an efficient and directed flow of liquid reagent from the main body 302 to the neck portion 303 for a colorimetric reaction. The shape of the receptacle 301 is designed so that reagent chemical flows downward to a bottom end of the receptacle 301 (when the pouch is held in a vertical position), and then is at least partially wicked up by a swab pad 331 (as will be shown and discussed later) to react with any particle material on the swab pad 331. The entire receptacle 301 is packed into a small form factor for portability and handling.

The base 304a of the receptacle 301 main body 302 includes a bottom (or back) wall and a plurality of sidewalls extending upwardly from the bottom wall to peripheral side edges of the receptacle 301 so as to define at least one chamber (also referred to as at least one walled cavity 321 discussed in detail below) which contains at least one ampoule or capsule. Where multiple chambers are implemented, the multiple chambers may have openings, grooves, and/or channels such that the chambers can be in fluid communication with each other. For example, a first chamber and a second chamber may be in fluid communication with each other to ensure a colorimetric reaction occurs during a substance testing operation. The neck portion 303 also includes a bottom (or back) wall and a plurality of side walls extending upwardly from the bottom wall to the peripheral side edges of the receptacle 301.

Optionally, the cover 304b includes two sets of upper ribs 306 and two sets of lower ribs 307. The two sets of upper ribs 306 and the two sets of lower ribs 307 extend laterally across the receptacle 301 at spaced intervals so as to enhance exterior gripping of the receptacle. Each set of ribs includes a plurality of ridges that project inwardly toward an inner side of the based 304a and outwardly away from the cover 304b of the receptacle. The outwardly projecting ridges are designed to provide an exterior gripping surface for a user, and the inwardly projecting ridges are design to provide a reduced surface area contacting the ampoule 340 on an interior side of the cover 304b to assist the user 202 in rupturing, via a squeezing/breaking operation, at least one ampoule 340 inside the at least one chamber of the receptacle 301. In one embodiment, the upper ribs 306 contain fewer ribs than the lower ribs 307; although, any suitable number and size may be employed. In one embodiment, the entire cover 304b is transparent, while in another embodiment, only the neck portion 303 is transparent. Further, the ribs 306, 307 may be configured and arranged in any suitable fashion, such as horizontal, vertical, or diagonal. In one embodiment, spike-like projections may be employed rather than ribs 306, 307 to grip the receptacle 301 and break the ampoule. The ribs 306, 307 also identify to the user 202 where to place their fingers on the receptacle 301 to rupture the ampoule 340. Additionally, the ribs 306, 307 provide additional strength to the material (e.g., plastic) of the receptacle 301, due to the ripple-like ribs 306, 307.

A proximal side of the receptacle 301 includes an opening 308 defined between topmost areas of the cover 304b and a bottom wall of the base 304a to allow for the removal and insertion of a swab 330 (also referred to as a swab insertion region as will be discussed in detail below). In embodiments, and as shown, e.g., in FIGS. 6A, 6B and 8, a surface of the insertion region defined by the bottom wall of the base 304a may be inclined downwardly relative to the cover 304b. The neck region 303 is provided on the opposite distal end of the receptacle 301.

The material of the cover 304b, if provided, can be plastic or other suitable material. The cover 304b can also be opaque, transparent or clear, or tinted. In embodiments, the cover 304b is clear or at least includes a clear window over the second chamber to frame the swab testing area for detection and colorimetric analysis. The thickness of the material of the base 304a and the cover 304b may be the same or different. In embodiments, the base 304a material thickness is thicker than the cover 304b material thickness to enhance a one way valve function of the receptacle 301 and prevent liquid that flows to the testing area from escaping or leaking out of the opening 308 provided at the proximal end thereof.

Optionally, the receptacle 301 also includes a mounting protrusion 309 that extends upwardly from a distal end of the neck portion 303 into an interior thereof so as to project toward the testing area. The mounting protrusion 309 acts to stop a downward insertion (toward the distal end of the receptacle 301) of the swab 330 (i.e., test swab) during a substance testing operation by the user, in order to prevent the pad 331 of the swab 330 from contacting an inside distal end of the receptacle 301 and being positioned in a pool of the released reagent, which could cause an adverse reaction between the substance on the pad 331 and the reagent if the pad 331 were saturated by the pooled reagent. Additionally, the mounting protrusion 309 prevents shadows which would otherwise be cast by the saturated swab 330 and unintentionally lead to color variance and ultimately inaccurate test results. In one embodiment, the mounting protrusion 309 extends upwardly from an inner wall of the cover 304b, but may alternately extend upwardly from the bottom wall 320 of the base 304a.

In one optional embodiment, a surface of the mounting protrusion 309 with which the pad 331 contacts is inclined away from the inside of the cover 304b toward the bottom wall 320 such that when the pad 331 is inserted into the receptacle 301, the pad 331 contacts the top of the surface of the mounting protrusion 309 and slides down the inclined surface away from the inside of the cover 304b.

The cover 304b includes the test window 310 located in the neck portion 303. The test window 310 is provided for observation of the testing area and for performing the colorimetric test and analysis. The test window 310 can be opaque, transparent or clear, or tinted. In embodiments, the test window 310 frames the swab testing area. In one embodiment, only the test window 310 of the cover 304b is transparent. The test window 310 may be raised from body of the receptacle 301 or even (flat) on the surface of the receptacle.

The material of the receptacle 301, apart from the cover 304b, can be, for example, cardboard, or any of the plastics, rubbers, polymers, elastomers, any combination thereof. The main body 302 can also be opaque, transparent or clear, tinted, white, black, etc. In embodiments, the main body 302 and the neck portion 303 (outside of the test window 310) is white so as to enhance accurate image detection. For example, the cover 304b may be formed from a matte clear plastic so that the camera on the computing device can easily capture an image of the pad 331 through, the swab 330 may be formed from white plastic, and the base 304a may be formed from black plastic, such that the black plastic provide contrast to the white color of the swab 330 against the black background of the base 304a for accurate color detection on the pad 331 by the application on the computing device 201.

The material of the receptacle 301 has sufficient strength, puncture resistance, elasticity so as to prevent puncture of the same even when the receptacle 301 is manipulated by the user 202 and the ampoules are crushed by the user 202 during a test operation to prevent shards of glass and/or plastic from puncturing the receptacle 301 and injuring the user 202. In addition, the receptacle is configured to enhance shock absorption so as to prevent inadvertent ampoule breakage during storage, transit or handling by the user prior to use.

According to one aspect of the present disclosure, prior to use, the receptacle 301 may be sealed in sterile bags in order to prevent contamination of the receptacle prior to testing of a test sample. In one embodiment, the receptacle 301 may be sealed in a metallic lined bag to keep light and contaminants out, and include a perforated tear strip to unseal and open the bag, according to an aspect of the present disclosure. While the receptacle 301 in FIG. 3 is shown as a substantially rectangular container having a tapered end on one longitudinal side, any suitable shape may be employed. For example, the receptacle 301 may be rectangular, circular, triangular, polygonal, etc. The receptacle 301 may have no taper, a taper on one end, or tapered on both ends.

The receptacle 301 is configured to test either trace or bulk samples, and is operable with computing devices, such as mobile devices, tablets, and smartphones. In an embodiment where the receptacle 301 is tapered on both ends, each end may include a separate testing area. In another aspect, a reaction between a targeted substance and a reagent may be observed by a naked eye of the observer. Thus, a computing device is not necessary according to this aspect. For example, by visually observing the color of a reaction between the targeted substance and the reagent, the user can see whether a positive test is detected, e.g., if the reaction between the targeted substance and the reagent is red, then the presence of cocaine is positive; and if no color reaction is observed or if the color is anything but red, then the presence of cocaine is negative.

At least one label on the receptacle 301 and/or cover 304b may contain at least one identification code (e.g., a Quick Response Code™ or QR CODE™) 311 which is specially placed, e.g., aligned, at a predetermined distance from the pad 331 of the swab 330 in the test window 310 of the pouch 301, so that the application on the computing device 201 (e.g., smartphone, smartglasses, smartwatch, tablet, etc.) can identify or approximate the exact location of the test sample on the pad 331 in the receptacle 301, so that the analysis of the trace material on the swab 330 can be analyzed.

The identification code 311 on the receptacle 301 serves at least three purposes. First, the identification code 311, when read by an application on the computing device 201, identifies to the application on the computing device 201 the specific test to be conducted. That is, the reagents for a test for one class of explosives test may be different that the reagents for another class of explosives, for other illicit drugs, for contaminated water, etc. Thus, one receptacle 301 may contain reagents for the detection of illicit drugs, while one receptacle 301 may contain reagents for the detection of certain classes of explosives. In one embodiment, the receptacle 301 may contain reagents in one ampoule for the detection of illicit drugs, and reagents in a second ampoule for detection of a certain class of explosives. Alternately, the receptacle 301 may contain one ampoule for detection of certain explosives and another ampoule for detection of other explosives. Thus, with appropriate identification and/or labelling on the receptacle 301, the user 202 can select from a plurality of available pouches and rupture one or both ampoules as required for detection of a suspected substance. For example, if the user 202 would like to test a substance for cocaine, the user would select a receptacle 301 identified as that used for cocaine, indicating that the ampoule(s) contain the particular reagent(s) to detect cocaine. Similarly, pouches having the appropriate reagents are provided for other drugs, explosives such as ammonium nitrate, drinking water contaminants, etc.

The identification code 311 contains information to let the application on the computing device 201 know which algorithm to run during analysis based on the colorimetric test to be performed, based on the targeted substance. It could also contain manufacturing date and lot number to use by the application to ensure that the receptacle 301 is not using expired reagents. If the application detects that a pouch contains expired reagents, then the application will send an audio and/or visual warning to the user 202, allowing the user 202 to conduct the test with a non-expired pouch.

Secondly, the identification code 311 provides manufacturing tracking information such as the lot number or date code of when the particular receptacle 301 was made, which is read by the camera on the computing device 201 and obtained by the application.

Additionally, the identification code 311 provides an alignment feature, in that the application, via reading of the identification code 311 by the computing device 201, interprets reads the identification code 311 and determines the receptacle 301 is properly aligned and that the pad 331 containing the substance being tested is a predetermined distance below the identification code 311 (for example, 10 mm), i.e., such that the application knows the location of the pad 331, being a predetermined distance from the identification code 311 when the swab 330 is inserted into the receptacle 301. For example, the size of the identification code 311 is measured at a distance that the identification code 311 is from the computing device 201 when the identification code 311 is scanned by the application on the computing device 201. Based on the size of the identification code 311 when read by the application on the computing device 201, the application determines how big the testing window 310 is below the identification code 311 and adjusts to focus on just the testing window 310.

Of course, the identification code 311 may be situated in any suitable orientation with respect to the testing area, above, below, left, right, etc. Additionally, any suitable distance from the identification code 311 to the testing area may be employed, e.g., 1 mm-500 mm.

It is noted that the arrangement of the various structural elements may be provided in any suitable manner and arrangement, and is not limited to the specific configuration depicted.

Figure 4:
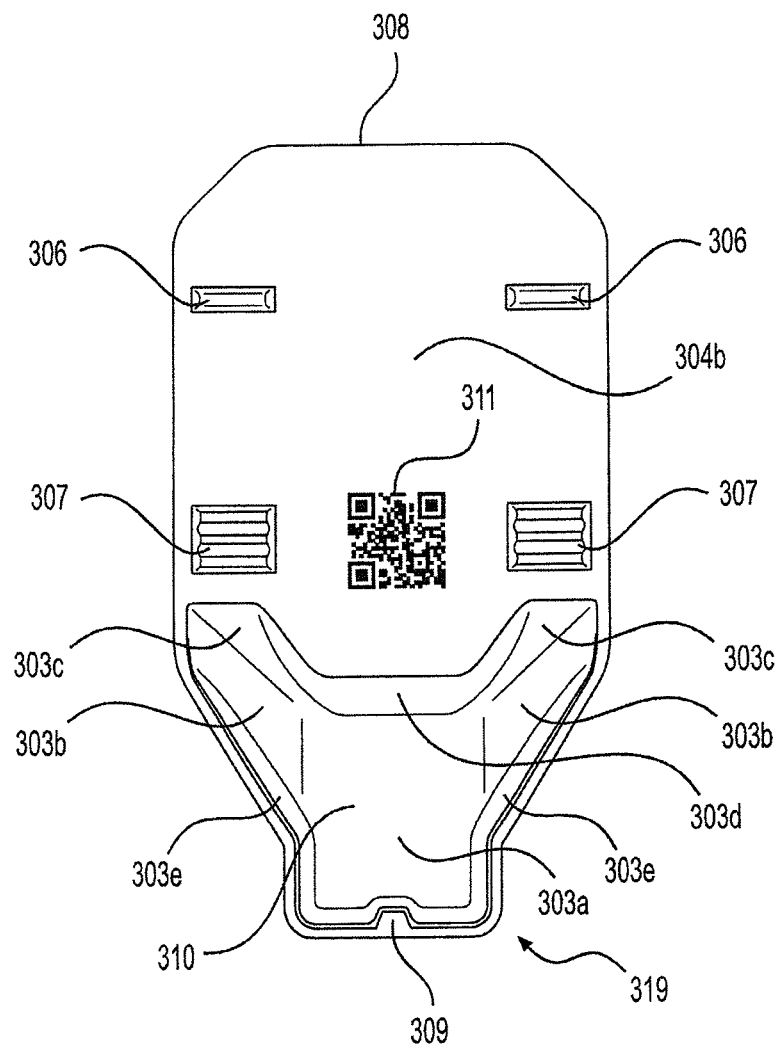
FIG. 4 is an exemplary front plan view of the receptacle, according to an aspect of the present disclosure.

FIG. 4 is an exemplary front plan view of the receptacle 301 showing the cover 304b, according to an aspect of the present disclosure. The receptacle 301 includes a testing area 319, defined within the neck portion 303, and framed by the testing window 310. A color calibration swatch 325 that includes at least one color calibration sample may also be provided adjacent the testing window 310, as will be discussed later. In one embodiment, two color calibration swatches may be provided. For example, a red, green, blue block and a white, gray, black block may be provided.

As shown in FIG. 4, the neck portion 303 optionally includes a top raised face 303a, left and right raised lower faces 303b, left and right raised upper faces 303c, a front raised face 303d, and left and right side raised faces 303e. In one embodiment, the left and right raised lower faces 303b, left and right raised upper faces 303c, a front raised face 303d extend outwardly from the cover 304b at angles not perpendicular to the cover 304b. Advantageously, the respective raised faces create a hollow reagent collection area (i.e., testing area 319), as will be show in greater detail in FIG. 9, which is configured to keep the inserted swab 330 spaced from the testing window 310 and prevent the swab 330 and/or pad 331 from adhering to the testing window 310 or an interior side of the cover 304b.

Figure 5:
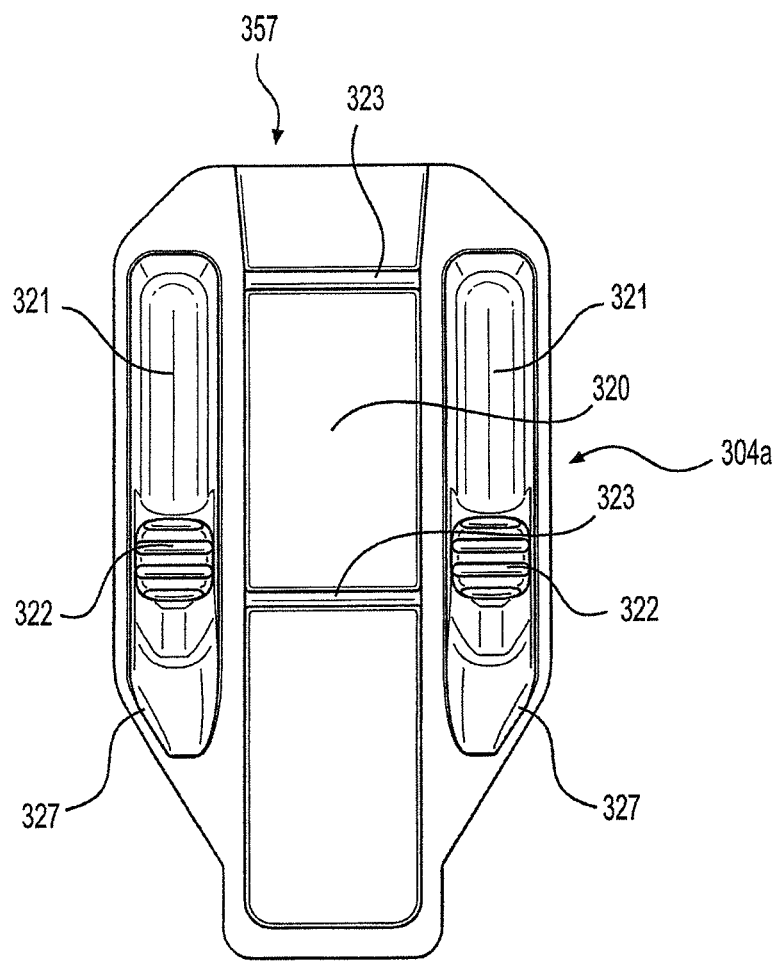
FIG. 5 is an exemplary rear plan view of the receptacle, according to an aspect of the present disclosure.

FIG. 5 is an exemplary rear plan view of the receptacle 301 showing an interior side of the base 304a, according to an aspect of the present disclosure. The base 304a includes a bottom wall 320, as discussed above. The bottom wall 320 contains at least one walled cavity 321 that extends outwardly and downwardly from the bottom wall 320 and configured to house the ampoule. The walled cavity 321 may include ribs 322 that project from a bottom wall thereof. Similar to ribs 306, 307, optional ribs 322 may extend laterally across the walled cavity 321 so as to enhance exterior gripping of the receptacle 301 and assist a user in rupturing, via a squeezing/breaking operation, the ampoule inside the walled cavity 321.

The bottom wall 320 also includes laterally extending support walls 323 that extend upward from the bottom wall toward the cover 304b to support the inserted swab 330 from a lower side thereof. This construction allows the inserted swab 330 to maintain spacing between the cover 304b and the bottom wall 320 of base 304a in the testing area 319 so as to ensure accurate substance detection and colorimetric analysis. The support walls 323 also serve as a guiding platform such that the inserted swab is accurately and securely positioned in the testing area 319 of the neck portion 303. The support walls 323 are also provided to prevent liquid released from the at least one ampoule into the testing area 319 from being drawn upwardly via capillary action toward the proximal end of the receptacle 301. As a result, the receptacle 301 is able to effectively control the flow of the reagents in the direction of the distal end of the receptacle 301 and the testing area 319 and prevent leakage out of the receptacle. Such a design enhances safety and clean-up during and after the colorimetric analysis is performed.

In one embodiment, the bottom wall 320 of the receptacle 301 will be either black or white to provide the swab pad sufficient contrast for viewing purposes, so that the color of the swab pad undergoing colorimetric reaction can be more accurately observed.

As shown in FIG. 5, the transition between the main body 302 and the neck portion 303 is Y-shaped, which assists with the flow of the reagent released from the ruptured ampoule into the testing area 319 and onto the pad 331. The walled cavity 321 includes tapered lateral walls 327 on an end toward the neck portion 303 to advantageously direct the flow of liquid from the ampoule to the testing area 319 in the neck portion 303. The lateral walls 327 incline upward from a lower side of the walled cavity 321 toward the bottom wall 320. The lateral walls 327, together with inner surfaces of the faces 303a-303e of the cover 304b, and tapered bottom walls 324 (FIG. 10), define a flow channel for reagent to flow toward and into the testing area 319 at a controlled flow rate. In embodiments the lateral walls 327 may incline gradually or in a stepped manner. The channel guide the flow of the reagent(s) to the testing window 310 area where it will flow over the pad 331.

Figure 6A:
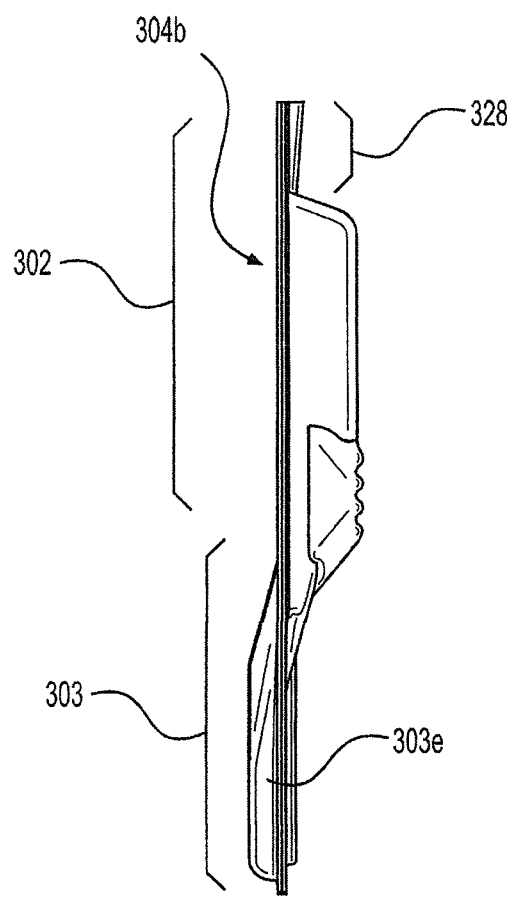
FIG. 6A is an exemplary right side plan view of the receptacle, according to an aspect of the present disclosure.

FIG. 6A is an exemplary right side plan view of the receptacle 301, according to an aspect of the present disclosure. As shown in FIG. 6A, the neck portion 303 of the cover 304b includes the side walls 303e and the side walls 303e extend upwardly relative to the main body 302 portion of the cover 304b. Thus, the area of the neck portion 303 of the cover 304b is stepped up from the main body 302 portion of the cover 304b. Advantageously, this configuration assists in prohibiting an inserted swab from contacting the cover 304b or testing window 310.

As also shown in FIG. 6A, in the raised window aspect of the present disclosure, at least one of the cover 304b and the bottom wall 320 includes a stepped portion defined by faces 303b, 303c, 303d to define a transition region between the main body 302 and the neck portion 303. The stepped portion may be inclined to allow fluid from the main body 302 to flow into and collect in the neck portion 303. In one embodiment, the volume of the main body 302 is larger than the volume of the neck portion 303. A height of the main body 302 is taller than a height of the neck portion 303. The difference in height allows an operator to more securely grasp the receptacle 301 and also minimizes the possibility of shards of glass and plastic from entering the neck portion 303 and interfering with a colorimetric test performed during the detection operation. As discussed above, certain of the side walls of the neck portion 303 may taper inwardly from the side walls of the main body 302 at the stepped portion transition region to define the Y-shape of the neck portion 303. The tapered walls also improve the speed in which the fluids of the ampoules interact with each other as well as guide the fluid into the neck portion 303. The tapered side walls also guide the swab 330 into a proper alignment position so as to enhance accuracy of the analysis portion of the detection operation.

The swab insertion region is defined at the proximal end of the receptacle 301 by a flanged section 328 of the main body 302. The flanged section 328 extends from an upper side of the main body 302 in a direction away from the neck portion 303. The flanged section 328 includes the opening 308 configured to receive a swab 330 or a bulk amount of detectable substance and allows the swab or bulk substance to pass through the flanged section 328, the main body 302 and into neck portion 303. The flanged section 328 is also configured to removably retain and guide the swab 330 through the upper side of the main body 302 and toward neck portion 303 such that the swab pad 331 is fully retained and aligned within the testing area 319. The flanged section 328 may also serve as a one way valve so that reagent released from the ruptured ampoule and is drawn, via capillary action, past support walls 323 toward opening 308 is prevented from exiting through the opening 308. This construction enhances safety to the operator as well as cleanliness for disposal of the receptacle 301. Furthermore, the flanged section 328 may include a resilient hinge section (e.g., at a transition region between a proximal side wall of the walled cavity 321 and the flanged section 328) that has sufficient flexibility relative to the main body 302 and neck portion 303 so that a user may grasp the flanged section 328 to shake the main body 302 during the colorimetric test portion of the detection operation and to allow the reagent released in the main body 302 to flow into the neck portion 303.

Figure 6B:
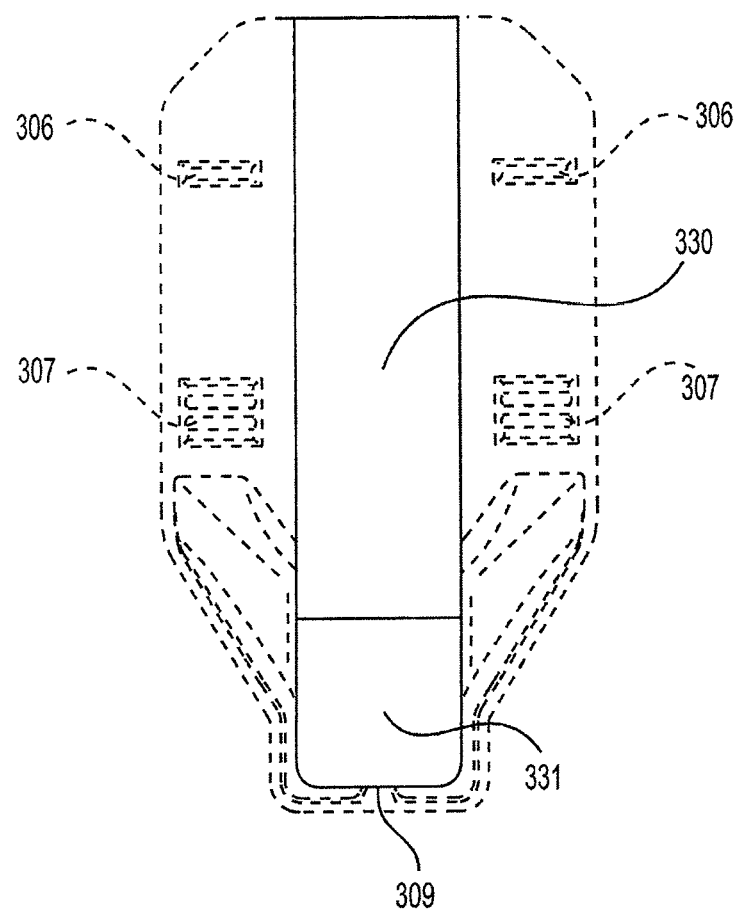
FIG. 6B is an exemplary plan view of the inside of the cover with a swab inserted in the receptacle, according to an aspect of the present disclosure.

FIG. 6B is an exemplary plan view of the inside of the cover with a swab inserted in the receptacle, according to an aspect of the present disclosure. The optional mounting protrusion 309 extends upwardly from a distal end of the neck portion 303 into an interior thereof so as to project toward the testing area 319. The mounting protrusion 309 acts to stop a downward insertion (toward the distal end of the receptacle 301) of the swab 330 (i.e., test swab) during a substance testing operation by the user, in order to prevent the pad 331 of the swab 330 from being placed in a pool of the released reagent, which could cause an adverse reaction between the substance on the pad 331 and the reagent if the pad 331 were saturated by the pooled reagent.

Figure 7:
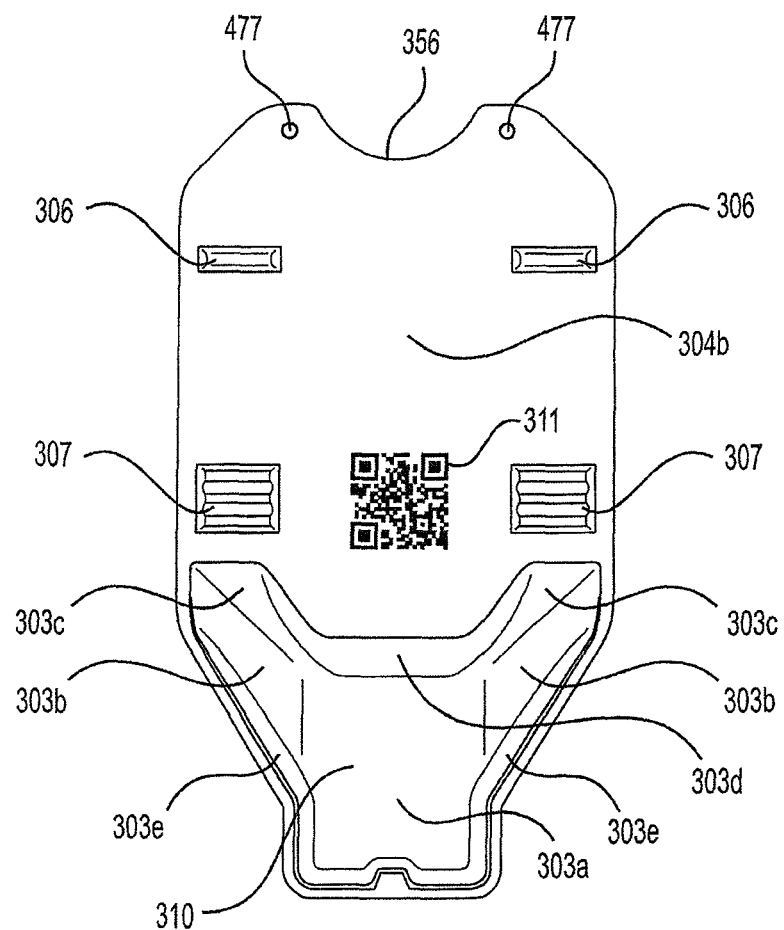
FIG. 7 is an exemplary front plan view of an alternate embodiment of the cover of the receptacle, according to an aspect of the present disclosure.

FIG. 7 is an exemplary front plan view of an alternative embodiment of the cover 304b of the receptacle 301 that includes a half-moon shape, according to an aspect of the present disclosure. The cover 304b includes a half-moon shaped recess 356, partially exposing a proximal tip of an inserted swab 330, in order to help the user 202 grip and grasp and guide the swab 330 out of and into the receptacle 301. For example, the half-moon recess 356 provides for partial exposure of the swab 330 when it is placed in the receptacle 301, so that the user 202 can use one or more fingers to place onto the end of the swab 330 and withdraw the swab 330 from the receptacle 301. While a half-moon shaped recess 356 is shown, it is noted that the shape of the recess may be formed of any suitable shape that would allow the user 202 to grasp the swab 330 for removal from the receptacle 301.

The cover 304b includes air holes 477 on the top left and top right of the cover 304b. The air holes 477 permit equalization of pressure above and below where the chemicals flow to the swab pad 331. By virtue of the equalization of the pressure, reagents are permitted to flow to cover the entire pad 331, regardless of differences in chemical viscosity in the various different reagents used in the different tests for targeted substances. The air holes are aligned with tunnels or channels 478, as will be discussed in FIG. 8A.

Figure 8A:
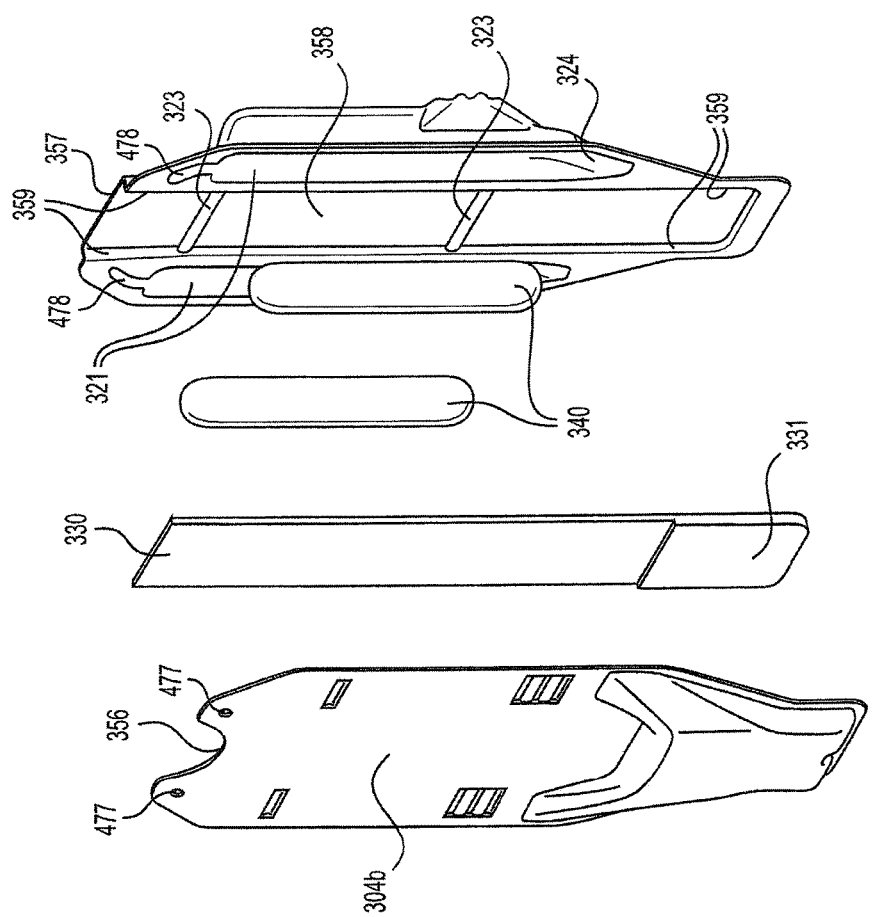
FIG. 8A is an exemplary right side exploded view of the alternative embodiment of FIG. 7 of the receptacle, according to an aspect of the present disclosure.

FIG. 8A is an exemplary right side exploded view of the receptacle 301 shown in FIG. 7, as a detection kit, according to an aspect of the present disclosure. The receptacle/detection kit 301 includes a swab 330 having a pad 331 at one longitudinal end of the swab 330. In embodiments, the swab 330 has a length substantially similar to a length of the receptacle 301; although, the swab 330 may be shorter in other embodiments. When fully inserted into the receptacle 301, the pad 331 is positioned within the testing area 319 of the neck portion 303. At least one ampoule 340 is positioned in a respective walled cavity 321, where the ampoule 340 is retained in place. In one aspect, the walled cavity 321 may be formed from a thicker material (e.g., plastic) than the remainder of the receptacle 301, to allow for the rupturing of the ampoule 340 while preventing shards of the ampoule 340 material (e.g., glass) from piercing the plastic.

When the ampoule 340 is ruptured by a user via a compressive external force applied to the receptacle 301, chemical reagent within the ampoule 340 is dispersed by, for example, the magnitude of the compressive force, the pull of gravity and guided via the tapered interior cavity walls 327 to the testing area 319. The receptacle 301 may contain markings to indicate to the user where the compressive force is to be applied to the receptacle 301. Such markings may be provided at areas corresponding to the ribs 306, 307, 322.

The ampoules 340 contain one or more chemicals (such as reagents) that react with test substances to produce a color. Examples of one or more chemicals are well known in the art. The ampoules 340 include a sealed capsule that contains the reagents. The ampoules or capsules 340 may be made of, for example, glass, plastics such as polypropylene, or other suitable materials to ensure consistent, reliable rupture during a detection operation.

The receptacle/detection kit 301 contains ampoules 340 with the reagents needed for the colorimetric reaction. Once a swab 330 containing material to be tested is reinserted into the receptacle 301, the user 202 will squeeze the receptacle 301 with sufficient force to rupture the ampoules causing the reagents, with the force of gravity, to travel to the bottom tapered neck portion 303 of the receptacle 301, when the receptacle 301 is held upright, although the same result can be obtained even if the receptacle 301 is held at an angle relative to the upright position (e.g., the receptacle 301 is held at a 45° angle relative to the upright position or even horizontally). In certain implementations, the user 202 may sequentially break multiple ampoules 340 resulting in sequential chemical flows. In one embodiment, protective sleeves are provided in the detection kit that extend around the ampoules to secure the ampoules in place in the main body 302 and so as not to injure the user 202 when the user ruptures the ampoules manually (with his/her hands). Advantageously, the user 202 is protected from fragments of glass or plastic that may otherwise pierce the receptacle and cut the skin of the user 202.

FIG. 8A also shows that the bottom wall 320 includes a recessed entrance 357, defining a portion of the swab insertion region. The recessed entrance 357 extends the length of the flange section 328. At the transition region (e.g., at the resilient hinge section) the recessed entrance transitions into a recessed track 358, both of which help the user guide the swab 330 into the receptacle 301. In embodiments, one of the support walls 323 defines a separation boundary that separates the recessed entrance 357 from the recessed track 358. In embodiments, a depth of the recess at the entrance 357 is greater than a depth of the recess at the track 358. In embodiments, the support walls 323 have a height that is less than the depth of both recesses.

The recessed entrance 357 and track 358 each include sidewalls 359 configured to guide the swab 330 into proper alignment within the receptacle 301. The sidewalls 359 are tapered outwardly toward the opening 308 to provide a flange-like receiving opening for the swab 330. Once the swab 330 is inserted past the tapered section of the sidewalls 359, the sidewalls 359 then become substantially parallel to a longitudinal length of the receptacle 301 to guide the swab 330 to the neck portion 303 and into the testing area 319. Advantageously, these guiding features help the user 202 properly guide the swab 330 into the receptacle 301 in a secure and speedy manner. In addition, the guide features also serve as a storage compartment for the swab 330 before and after a detection test is performed. The storage compartment minimizes the risk of contamination of the pad 331 before and after a detection test is performed. The swab 330 is provided in the receptacle 301 prior to the detection test to minimize exposure of the pad 331 to the external environment to prevent contact with foreign surfaces or substances that may compromise accurate detection of substances being tested. After the detection test is completed, the guide features help retain the swab 330 within the receptacle for easy clean-up. In embodiments, the receptacle 301 may have sufficient flexibility to widen opening 308 to allow a bulk substance to be inserted into the testing area 319. Here, the guide features may define a slot extending from the opening 308 to the test window 310 to allow for the bulk substance to be inserted and tested. In other embodiments, the one or more ampoules may be formed of a unitary/integral structure with the receptacle 301, e.g., it is contemplated that the ampoules may be defined by a portion of the receptacle 301 itself when the receptacle 301 is manufactured, e.g., when the receptacle 301 is formed during a molding process.

In embodiments, the receptacle 301 includes at least one reagent ampoule 340 and may or may not include a test swab 330. Indicia on an outer surface of the receptacle 301 include numerical or suitable identifiers associated with the numbers of and locations of ampoules in the pouch. Additionally, the outer surface of the receptacle 301 and/or cover 304b includes the identification code 311 a predetermined distance to the testing area 319. In embodiments, the predetermined distance is measured as a distance from a position of the identification code 311 to a position of the testing window 310 framing the testing area 319. In other embodiments, the predetermined distance is measured as a distance from a position of the identification code 311 directly to a position of the testing area 319 and/or the pad 331. In still other embodiments, the testing area 319 of receptacle 301 may be exposed without a testing window specifically framing or covering the testing area 319.

Air channels 478 are provided to receive air from air holes 477. The air holes 477 and the air channels 478 are in fluid communication and permit equalization of pressure above and below where the chemicals flow to pad 331 of the swab. The air channels 478 are also in communication with the cavities 321. By virtue of the equalization of the pressure, reagents are permitted to flow to cover the entire pad 331, regardless of differences in chemical viscosity in the various different reagents used in the different tests for targeted substances.

Figure 8B:
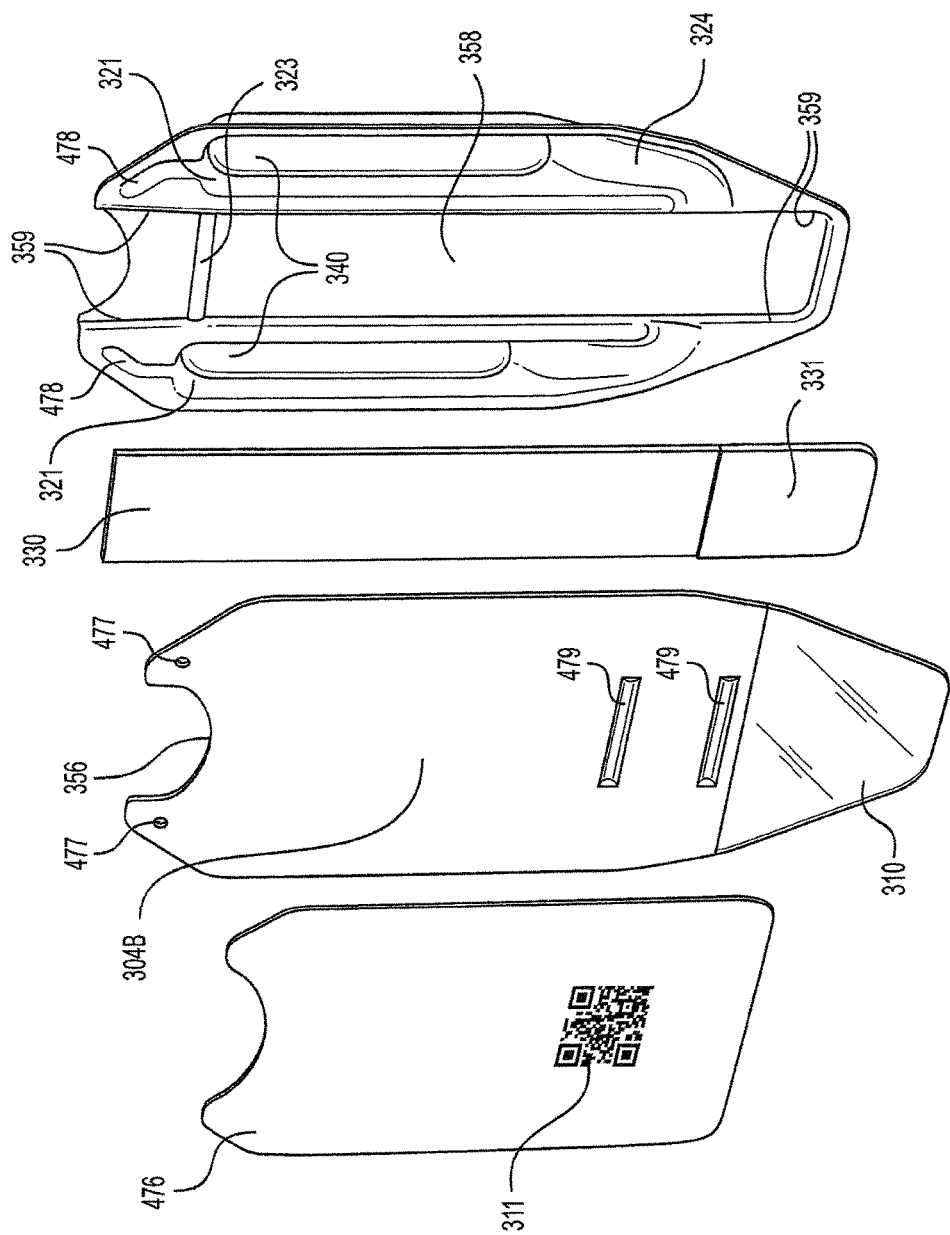
FIG. 8B is an exploded view of another embodiment of the receptacle, according to an aspect of the present disclosure.

FIG. 8B is another alternate embodiment of the receptacle, according to an aspect of the present disclosure. In this embodiment, the cover 304b including the window 310 is predominantly flat without a raised y-shaped neck portion 303. Thus, the swab 330 sits snuggly between the cover 304b and the bottom wall 320. By virtue of the snug fit, the flow of the reagents is increased because of the capillary action between the swab pad 331 and the cover 304b or window 310, as the solution flows from the crushed ampoules 340 to the detection area where the pad 331 is positioned in the recessed track 358.

On the cover 304b, the window 310 is transparent in order to allow an image of a reaction between the reagents and the targeted substance on the swab pad 331 to be captured by the computing device 201. The cover 304b includes a half-moon shaped recess 356, partially exposing a proximal tip of an inserted swab 330, in order to help the user 202 grip and grasp and guide the swab 330 out of and into the receptacle 301. The bottom wall 320 includes the sidewalls 359, the cavities 321 for the ampoules 340, the recessed track 358 for the swab 330, the support wall 323, the air channels 478, and the channels 324.

To help facilitate the flow of the reagent to the detection area where the pad is, the channels 324 are defined on the inside of the bottom wall 320 to guide the reagent downwardly to the recessed track 358 and the detection area to contact the pad 331. As shown in FIG. 8B, the channels 324 extend from the cavities 321 to the recessed track 358. In an alternative embodiment where no recessed track 358 is provided, the channels 324 extend from the cavities 321 to the detection area where the pad 331 is positioned.

A label 476 is provided which include the identification code 311 and color calibration swatch 325. Cross beam walls 479 are provided to keep solution from traveling up the swab 330 and leaking out the top with capillary action. In the alternative embodiment of FIG. 8B, a cover 476 with the identification code 311 is provided. The window 310 is a transparent window below the cross beam walls 479, through which the swab can be observed, and captured by camera of the computing device 201.

In the embodiment of FIG. 8B, cross beam walls 479 are provided and only one support wall 323 is provided, both of which prevents reagents from travelling upwardly and leaking out through the top of the receptacle.

As with the embodiment of FIG. 8A, air holes 477 and air channels 478 are provided. The air holes 477 and the air channels 478 are in fluid communication and permit equalization of pressure above and below where the chemicals flow to pad 331 of the swab. The air channels 478 are also in communication with the cavities 321. By virtue of the equalization of the pressure, chemical are permitted to flow to cover the entire pad 331, regardless of differences in chemical viscosity in the various different reagents used in the different tests for targeted substances. Thus, the air holes 477 in conjunction with the air channels 478, aid in pressure equalization and solution flow.

Figure 9:
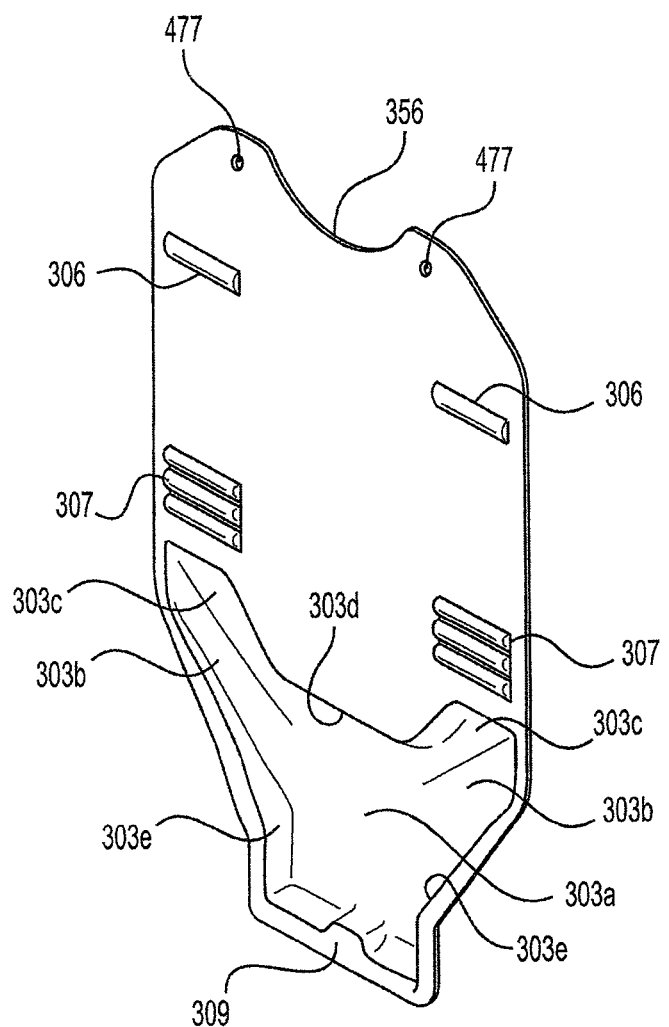
FIG. 9 is an exemplary right side perspective view of an inside view of the cover 304b, of the embodiment of FIG. 7, according to an aspect of the present disclosure.

FIG. 9 is an exemplary right side perspective view of an inside view of the cover 304b, of the embodiment of FIG. 7, according to an aspect of the present disclosure. As shown in FIG. 9, the ribs 306 and 307 project in a substantially perpendicular manner from a rear side of the cover 304b. The mounting protrusion 309 may be defined as a part of an interior lower wall of the cover or part of an interior lower portion of the testing window 310, or both. In this regard, the mounting protrusion may extend upwardly from inside the lower wall of the cover 304b adjacent the testing window 310, upwardly from a lower side of the testing window 310, or from both, so that the lower end of the swab 330 is prevented from contacting the lower wall of the cover 304a and/or testing window 310. It is contemplated that the mounting protrusion could be defined as a part of an interior lower wall of the base 304a and project upwardly from the interior lower wall thereof as well. By virtue of the configured relationship between the top raised face 303a, the left and right raised lower faces 303b, the left and right raised upper faces 303c, the front raised face 303d, and the left and right side raised faces 303e, a hollow recessed section is formed on the rear side of the inside of the cover 304b such that the inserted swab 330 is spaced from the test window 310.

The inserted swab 330, which is positioned along track 358 so as to be retained within the receptacle 301, is thus prevented from contacting the testing window 310, since the raised faces 303a-303e of the neck portion 303 create a space in front of the swab 330. Thus, during a detection test, while the pad 331 will absorb reagent, neither the pad 331, nor the swab 330, will contact or adhere to an inside surface of the testing window 310 or cover 304b in the neck portion 303. It is contemplated that the cover 304b may optionally include a ramp structure that including an inclined surface that projects from an interior side of the cover 304b and extends back toward the base 304a to guide the swab 330 in a direction away from the testing window 310, as the swab 330 is slid downwardly in the receptacle 301. When the swab 330 is inserted, the ramp structure is designed to ensure that the lower end of the swab 330 is prevented from contacting the lower wall of the cover 304b and/or testing window 310. Thus, a space is created between the pad 331 of the swab 330 and the cover 304b and/or testing window 310. This prevents a capillary effect where excess reagent is caught between the pad 331 and the cover 304b and/or testing window 310, which could dilute the reaction occurring on the pad 331 and reflect light when attempting to capture the reaction on the pad 331 with the computing device 201. Additionally, the air holes 477 are in fluid communication with the air channels to permit equalization of pressure above and below where the chemicals flow to pad 331 of the swab.

Figure 10:
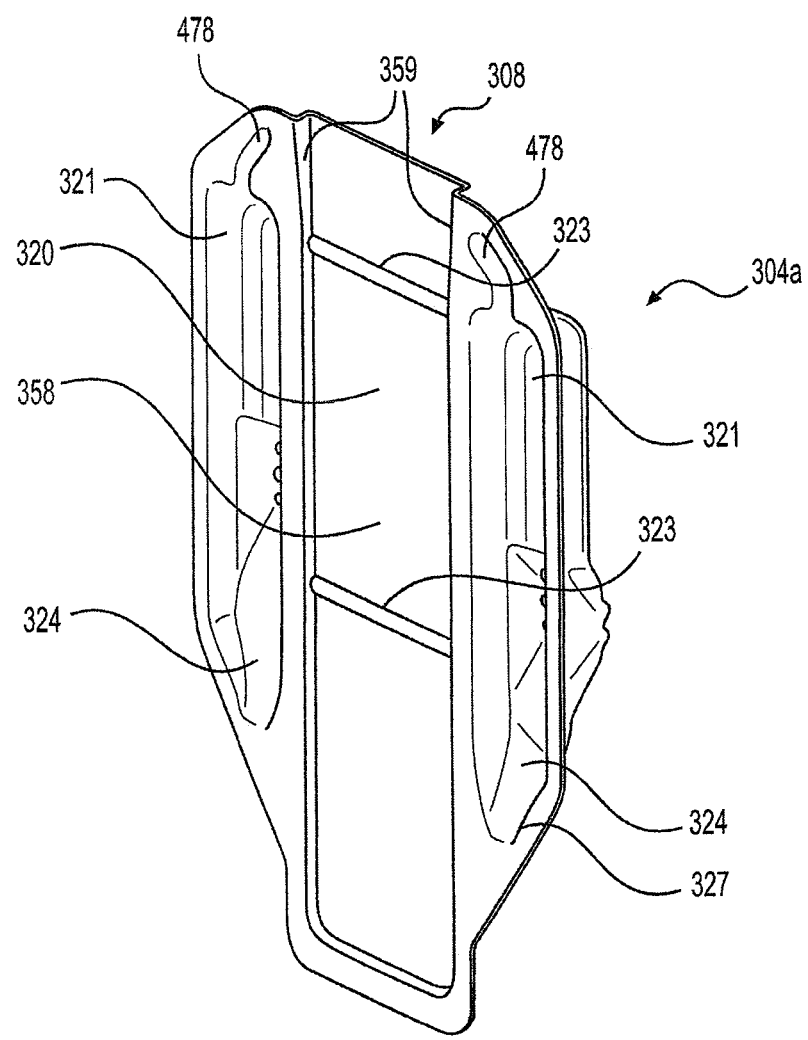
FIG. 10 is an exemplary right perspective view of an inside of the bottom wall of the receptacle, according to an aspect of the present disclosure.

FIG. 10 is an exemplary right perspective view of an inside of the bottom wall of the base 304a, according to an aspect of the present disclosure. As shown in FIG. 10, the support walls 323 extend upward from the bottom wall 320 to prevent the flow of liquid reagent from the ruptured ampoules 340 from traveling upwardly toward the opening 308 of the receptacle 301 due to capillary action of the liquid between the cover 304b and the swab 330 and between the base 304a and the swab 330. The support walls 323 extend across the recessed track 358 and may be semi-circular or squared (or any suitable shape to support the inserted swab 330 and prevent liquid from traveling toward opening 308). Essentially, the walls 323 push the swab against the cover 304b and create a seal to prevent liquid from passing the walls 323 and leaking out of the receptacle 301. In another embodiment, wells or troughs, rather than walls 323 may be used to achieve the same effect.

Air channels 478 are provided to receive air from air holes 477. The air holes 477 and the air channels 478 are in fluid communication with each other and permit equalization of pressure above and below where the chemicals flow to pad 331 of the swab. The air channels 478 are also in communication with the cavities 321. By virtue of the equalization of the pressure, reagents are permitted to flow to cover the entire pad 331, regardless of differences in chemical viscosity in the various different reagents used in the different tests for targeted substances.

Figure 11A:
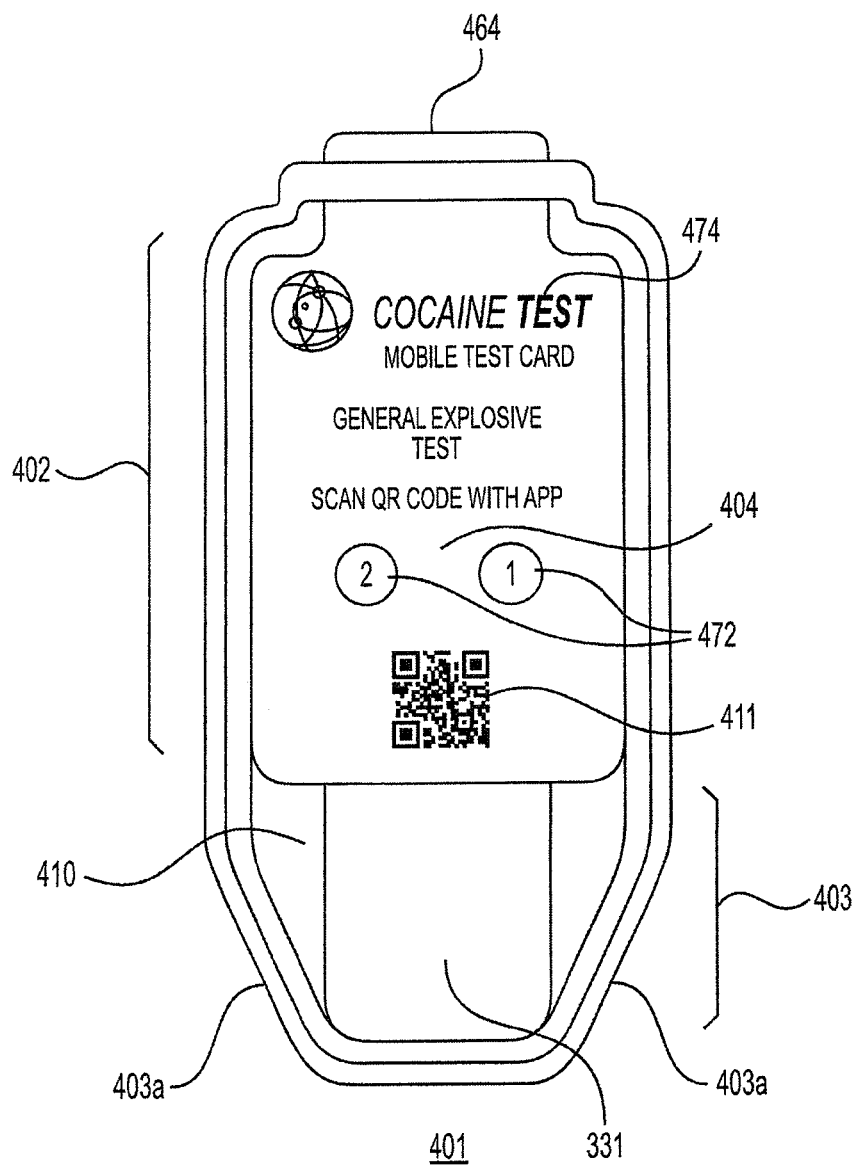
FIG. 11A is an exemplary front plan view of an alternate embodiment of the receptacle, according to an aspect of the present disclosure.

FIG. 11A is an exemplary front plan view of an alternative embodiment of a receptacle 401, according to an aspect of the present disclosure. The receptacle 401 includes a main body 402, a neck portion 403 extending from the main body 402, side walls 405, and a cover 404 sealed to and extending along peripheral upper side edges of the main body 402 and the neck portion 403. The receptacle 401 also includes a bottom wall 420 (see FIG. 11B) provided opposite the cover 404 so as to define an interior of the receptacle 401. In one embodiment, the main body 402 houses an upper first chamber and the neck portion 403 houses a lower second chamber. The neck portion 403 extends from the main body 402 in a tapered manner toward a lower end of the receptacle 401.

Figure 11B:
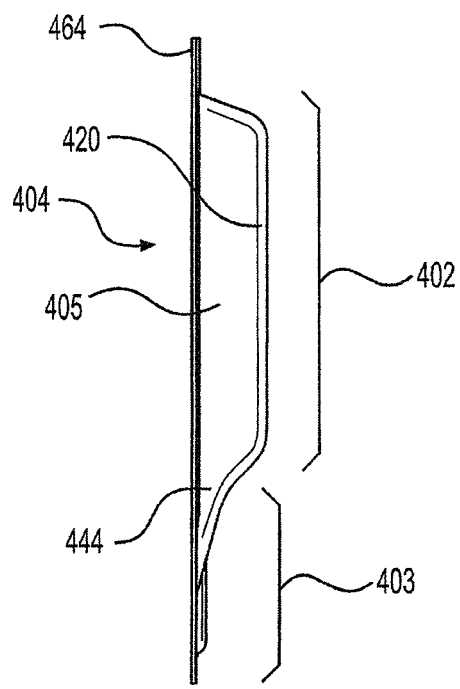
FIG. 11B is an exemplary right side plan view of the alternate embodiment of the receptacle, according to an aspect of the present disclosure.

As shown in FIG. 11B, one of the cover 404 and the bottom wall 420 includes a stepped portion 444 to define a transition region between the chambers. The stepped portion 444 may be inclined to allow fluid from one chamber to flow into and collect in another chamber. In one embodiment, the volume of a first chamber is larger than the volume of a second chamber. The height of the first chamber from the bottom wall 420 to the cover 404 is taller than the height of the second chamber from the bottom wall 420 to the cover 404. The difference in height allows an operator to more securely grasp the receptacle 401 and also minimizes the possibility of shards of glass and plastic from entering the second chamber and interfering with a colorimetric test performed during the detection operation. Certain side walls of the second chamber may taper (tapered walls 403a) inwardly from the side walls of the first chamber at the stepped portion 444 transition region. The tapered walls 403a also improve the speed in which the fluids of the ampoules interact with each other as well as guide the reagent into the second chamber. The tapered side walls 403a also guide the swab 330 into a proper alignment position so as to enhance accuracy of the analysis portion of the detection operation.

As also shown in FIG. 11A, a flange section 464 extends from an upper side of the main body 402. This flange section 464 assists the user in guiding the swab 330 out of and into the receptacle 401 toward a test window 410 when the swab 330 is fully inserted. The flange section 464 extends from the main body 402 in a direction away from the second chamber and the neck portion 403. The flange section 464 defines a slit opening configured to receive the swab 330 or a bulk amount of detectable substance and allows the swab 330 or bulk substance to pass through the flange section 464 to the second chamber for a detection operation. The flange section 464 is also configured to removably retain and guide the swab 330 into the main body 402 along the upper side of the first chamber and toward a bottom side end of the second chamber such that the swab 330 is fully retained and aligned within the second chamber. The flange section 464 may also serve as a one way valve so that reagent ruptured by the ampoule(s) 340 in the main body 402 is prevented from exiting through the slit opening. This enhances safety to the operator as well as cleanliness for disposal of the receptacle 401. Furthermore, flange section 464 may include a resilient hinge section (e.g., near the interface of the main body 402 and the flange section 464) that has sufficient flexibility relative to the main body 402 so that a user may grasp the flange section 464 to shake the main pouch body during the colorimetric test portion of the detection operation and to allow the reagent in the main body 402 to pool in the second chamber. The bottom wall 420 of the first chamber may be larger than the bottom wall 420 of the second chamber. The bottom wall 420 of the first chamber and the cover 404 may be flat surfaces such that multiple receptacles can be securely stacked on top of one another for storage or for transport.

In embodiments, the receptacle 401 includes markings 472 that identify to the user the location of ampoules 340 within the receptacle 401. Additionally, a test identifier 474 identifies to the user what test the particular receptacle 401 is configured for, e.g., explosive detection, drug detection. As with the previous embodiment, the receptacle 401 and/or cover 404 may contain at least one identification code 411 that operates in a substantially similar manner as that discussed above. As with the previously discussed embodiment, a color calibration swatch (not shown) may also be provided.

Similar to that described with respect to the receptacle 301, the receptacle 401 is configured to retain protective sleeves in the main body 402 that extend around the ampoule(s) 340 to secure the ampoule(s) 340 in place in the main body 402 and so as not to injure the user 202 when the user ruptures the ampoule(s) 402 manually (with his/her hands). Advantageously, the user 202 is protected from fragments of glass or plastic that may otherwise pierce the receptacle 401 and cut the skin of the user 202. In addition, the protective sleeve may include guide rails that guide the inserted swab 330 received from flange section 464 into the testing area.

In particular, the protective sleeve retains the ampoules 340 in a fixed position along the swab 330 insertion direction. In embodiments, the protective sleeve includes a top separation plate and two ampoule retention grooves extending from a lower side thereof to secure the ampoule(s) 340 in the protective sleeve. Both the separation plate and the retention grooves serve as a protection shield against shards of glass when the ampoules are crushed. In addition, because the ampoules are placed on a lower side of the separation plate, both the retention grooves and the separation plate minimize the amount of liquid reagent that that is inadvertently splashed by the ampoule breakage and absorbed on the test swab 330 outside of the swab test area 319 thereby corralling the reagent and directing the same toward the second chamber for mixing and reaction with the trace or bulk substance. The protective sleeve may also incorporate glass breakage features to allow for rapid and reliable breakage of the ampoules 340 during operation. For example, inner surfaces of the retention grooves may include breakage projections, etc. The sleeve may also include guide rails that extend upward from a top side of the separation plate toward the cover to provide additional spacing between the ampoules 340 and the cover 404 and to guide and align the swab 330 inserted into the main body 402 from the flange section 464 toward the second chamber in the neck portion 403 for testing. In other embodiments, it is contemplated that a protective sleeve may not be used, and instead a series of channel(s), formed in the receptacle 401, itself, may be employed that hold the ampoule(s) 340, and optionally, guide the swab 330. That is, a channel(s) could be formed in the receptacle 401 to retain the ampoules and prevent glass from piercing the receptacle 401.

The protective sleeve is resiliently deformable to its original shape thereby enhancing the ability of the protective sleeve to be manipulated to effectively rupture the ampoules 340 and retain the shards of glass in the first chamber. In this regard, the protective sleeve may be made of any suitable material to achieve such effects, e.g., any plastic, rubber, polymer, elastomers, etc.

FIG. 11B is an exemplary right side plan view of the alternate embodiment of the receptacle, according to an aspect of the present disclosure. The cover 404 or the bottom wall 420 includes a stepped portion 444 that defines the transition region between the chambers. The stepped portion 444 may be inclined to allow fluid from one chamber to flow into and collect in another chamber. For example, fluid traveling from a ruptured ampoule 340 will traverse the receptacle 301 and collect in the second chamber for a testing operation. As shown, the volume of a first (upper) chamber is larger than the volume of a second (lower) chamber. That is, the height of the first chamber from the bottom wall 420 to the cover 404 is taller than the height of the second chamber from the bottom wall 420 to the cover 404. Advantageously, the difference in height allows an operator to more securely grasp the receptacle 401 and also minimizes the possibility of shards of glass and plastic from entering the second chamber and interfering with a colorimetric test performed during the detection operation.

Figure 12A:
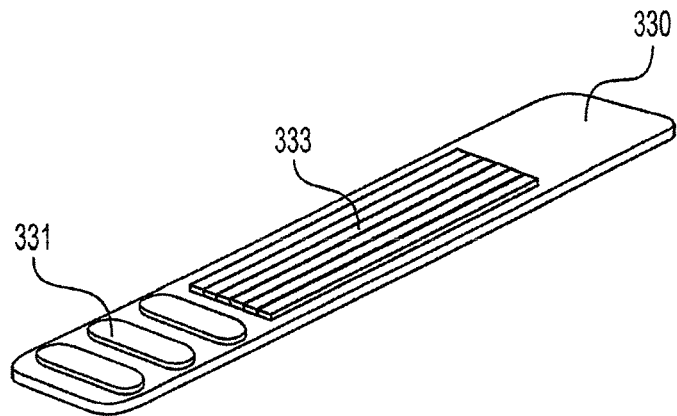
FIG. 12A is an exemplary view of a swab, according to an aspect of the present disclosure.
Figure 12B:
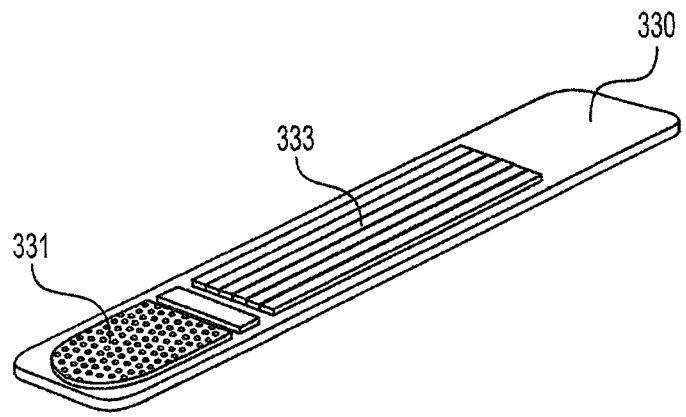
FIG. 12B is an exemplary view of a swab, according to an aspect of the present disclosure.
Figure 12C:
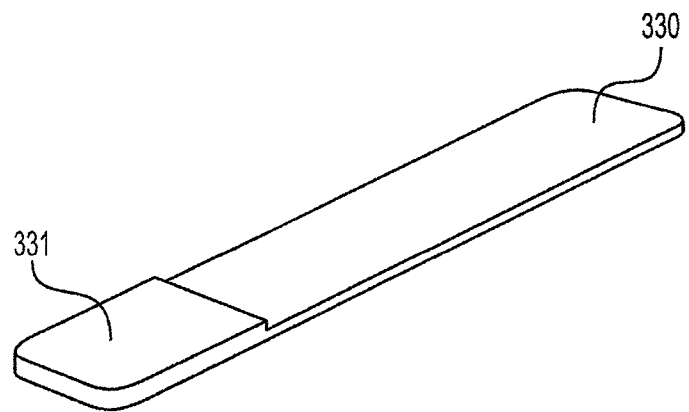
FIG. 12C is an exemplary view of a swab, according to an aspect of the present disclosure.

FIGS. 12A, 12B, and 12C illustrate various configurations for swab 330. The swab 330 is configured to be inserted and guided down in a distal direction of the receptacle 301 (401) to the testing area 319 of the receptacle 301 via entrance 357 and track 358, where it can be viewed. In FIG. 12A, the pad 331 contains a plurality of grooves. In FIG. 12B, the pad 331 contains a plurality of raised dots. In FIG. 12C, the pad 331 contains a smooth surface; although, any suitable texture may be provided on the pad 331.

The swab 330 can be employed by the user 202 to sample trace or non-visible material. That is, the user removes the swab 330 from the receptacle 301 and brushes the pad 331 of the swab 330 in the material to be tested, thus picking up residue on the pad 331 of the swab 330. While in one embodiment the swab 330 is removable from the receptacle 301, the swab 330 may also be integral with the receptacle 301, for example, able to only partially slide out of the receptacle 301 to expose the test surface. The swab 330 provides capability to perform trace detection of targeted substances. In one embodiment grooves 333 may be provided to provide an enhanced gripping surface for the user 202.

Advantageously, the test surface of the swab 330 includes at least one of a variety of patterns designed to collect trace amounts of material more efficiently than flat, planar surfaces. For example, the pad 331 of the swab may include grooves or raised patterns 331 of one or any combination of checking, zig-zags, diamonds, dots, triangles, v-grooves, cubes, squares, rectangles, circles, pyramids, chevrons, stars, polygons, etc. Additionally, the natures of the patterns would assist in the gathering of trace amounts of materials to be tested from non-uniform surfaces, porous surfaces, cracked surfaces, textiles, skin, etc. Another alternative swab design includes Q-TIPST™ style swabs.

The patterns, including the grooves aid in collecting material from a surface to be sampled onto the pad 331 of the swab 330. The patterns give the pad 331 surface features that help scrape material off a surface and become collected on the pad, affording the user enhanced trace collection ability. As used herein, trace amounts include both visible and non-visible particles, including those in the microgram, nanogram, or picogram range.

In one embodiment, a stronger color signal may be achieved along the grooves or raised portions, as a tendency of higher concentrations of trace substance would accumulate in the grooves or raised portions. In one embodiment, pad 331 is located on both longitudinal ends of the swab 330.

Figure 13:
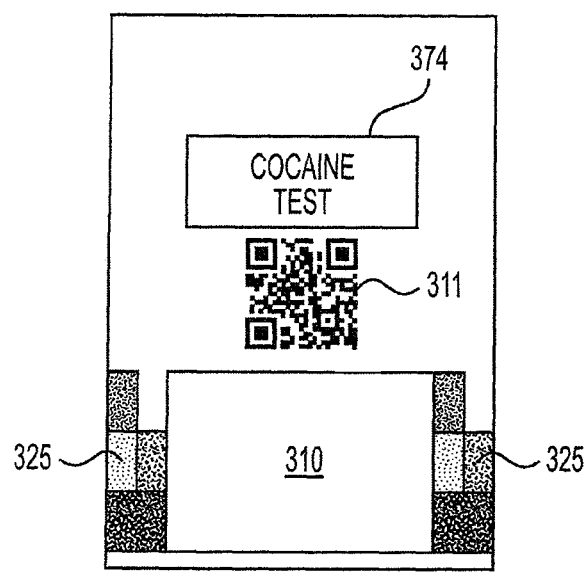
FIG. 13 is an exemplary view of a label that may be affixed to the front cover of the receptacle, according to an aspect of the present disclosure.

FIG. 13 is an exemplary view of a label that may be affixed to the front cover, according to an aspect of the present disclosure. In one embodiment, after opening the application on the computing device 201, a box or other suitable shape is displayed on the display of the computing device 201. The user 202 then aligns the box with the identification code 311 on the receptacle 301. The application then performs a check to determine with the identification code 311 is within the box on the user display. If the identification code 311 is aligned with the box displayed by the application on the user display, the application signals the camera to capture the image. After capturing the image, the application begins analyzing the colorimetric reaction. In one embodiment, the identification code 311 and at least one color swatch 325 are printed onto the cover 304b of the receptacle 301. As noted above, the pad 331 containing the substance being tested is a predetermined distance below the identification code 311 (for example, 10 mm), so that the camera can capture color of the chemical reaction between the reagent(s) and the substance.

While a QR Code™ may be employed as the identification code 311, other codes and/or techniques may be employed, including near field communication (NFC), iBeacon, clickable paper, SnapTag, augmented reality, GOOGLE™ Goggles, universal product code (UPC), radiofrequency identification (RFID), image recognition, MICROSOFT™ Tag, barcode, optical character recognition (OCR), machine readable indicia, image, code, graphical representation, symbol, label, pattern, emblem, stamp, logo, etc., including any combination thereof.

It is noted that any color pattern or other pattern that would be recognizable by OCR may be employed. In one aspect, the user 202 may have to line up a box with a printed box on the receptacle 301. OCR may be used to identify unique shapes or colors on the label in order to get the same info and also use for alignment. For example, a box displayed by the application on the computing device 201 may have to be aligned with a corresponding box on the pouch 301, to achieve the correct alignment. In another embodiment, RFID and/or NFC technology in the computing devices may read a unique tag on the receptacle 301 to retrieve at least the test identification information. Thus, the computing device 201 could simply locate the swab 331 with OCR for alignment.

In one embodiment, the application on the computing device 201 uses a white sample near or in lieu of the swatch 325 to perform correct color calibration. Thus, the swatch 325 is optionally provided on the label.

In an embodiment, one or more color swatches 325 of reference colors may be provided to the left and/or right of the testing area so that the application on the computing device 201 can calibrate true color for the colorimetric test, rather than a color anticipated by the application based on the type of test being performed. That is, the application is able to determine lighting conditions during the test and adjust based on the swatches 325 to obtain true colors. Algorithms in the application provide color balancing by taking measurements of the reference colors on the swatches 325 during the test.

Advantageously, the application can accurately perform the colorimetric test in all conditions, including various lighting conditions, e.g., dark conditions, bright conditions, conditions affected by emergency vehicle lights, etc. In one embodiment, the color of the reaction between the substance being testing and the reagents can be accurately measured and/or adjusted in response to a known color sample in the form of the swatch.

In one embodiment, the color swatches 325 include red, green, and blue rectangular swatches in a vertical orientation on one side of the testing area and blue, green, and red rectangular swatches on the other side of the testing area. Between the red, green, and blue swatches and the testing area, white, gray, and black rectangular swatches are provided. It is noted that any order, number, shape, colors, and positioning of the swatches may be employed.

In one embodiment, gray is the sole swatch adjacent the testing area, as gray is exactly at the midpoint between white and black therefore allowing for a calibration to both and all colors. In another embodiment, ambient light may be correlated to the measured light and already calculated effect on colors.

In another embodiment, color balancing can be done without any calibration swatches or reference colors. In this regard, it is noted that many computing devices have this functionality built into the camera. In another embodiment, the color balancing may be based upon the white area around the testing window 310 and/or around the swatches 325.

In another embodiment, target color may be used directly. That is, if a certain test is known to turn from pink to light blue for positive, then a light blue swatch could be included on the pouch for the application to look for a match for that color on the pad. As another example, if ambient red tinted light causes any blue color to look purple, then the target reference color swatch is also made to look purple so that the application would know to look for purple instead of blue.

In one embodiment, at least one swatch 325 is affixed to the receptacle 301 and/or cover 304b with a label. In an alternative embodiment, the swatches are printed directly onto the receptacle 301 and/or cover 304b. Any printing process may be employed including offset printing, rotogravure, flexography, letterpress, screen, electrophotography, inkjet, laser, transfer, etc.

In an alternative embodiment, an outer sleeve of cardboard or plastic may be provided and in which the computing device 201 may be inserted. The outer sleeve is configured to shield ambient light and/or align the receptacle 301 with respect to the camera on the computing device 201 when the receptacle 301 is inserted into sleeve (e.g., an external alignment tool for use with the computing device and the pouch). The sleeve is molded of any suitable material, including, cardboard, elastomer, polymer, etc. in a size and shape to fit over and conform to the computing device 201.

In embodiments, the receptacle 301 (401) includes the identification code 311 and tapered testing area at only one end thereof. However, in other embodiments, the tapered testing area may be provided on both longitudinal ends of the receptacle 301. In this regard, the receptacle 301 may be provided with ampoules on both sides (e.g., front and back) for multiple substance test capabilities. Thus, each receptacle 301 may be used for more than one test. For example, one or more ampoules may be provided on either side of the receptacle 301 for more than one test. In this embodiment, at least one identification code 311, at least one test area, at least one color calibration swatch 325, and at least one chamber may be provided on each side of the receptacle 301 to facilitate the testing of more than one sample. In embodiments, the ampoule(s) 340 on each side of the receptacle 301 may contain different reagents to test for different targeted substances, or alternatively, may contain the same reagents. In still other embodiments, one or more partitions may divide the receptacle 301 along the longitudinal direction so that multiple testing areas on the longitudinal end are defined to perform more than one test simultaneously. In still further embodiments, the receptacle 301 may be a double-sided pouch (with or without partitions as discussed above) so that features on one side of the receptacle 301 (e.g., the front) mirror the features on the other side of the receptacle 301 (e.g., the rear), thereby also allowing multiple tests to be performed on one or more samples by a single receptacle 301.

Figure 14:
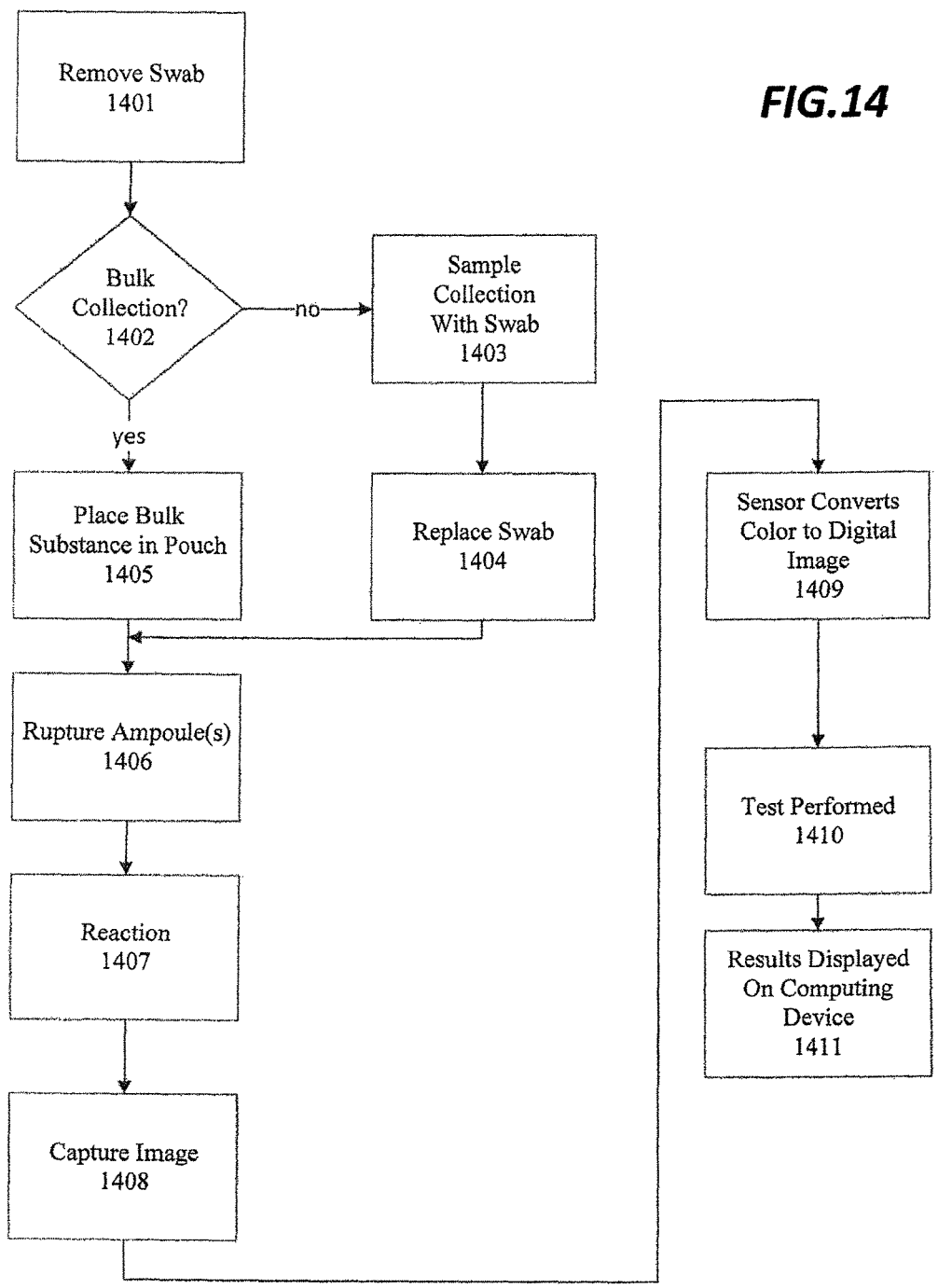
FIG. 14 shows an exemplary flowchart by which a determination of the presence of a chemical substance, element, compound is made, using at least one color reagent, according to one aspect of the present disclosure.

FIG. 14 shows an exemplary flowchart by which a determination of the presence of a chemical substance, element, compound is made, using at least one color reagent, according to one aspect of the present disclosure. In operation, the user 202 opens the sealed receptacle 301, removes the swab 330 from the receptacle 301, and swabs the substance to be detected with the pad 331. Alternatively, for bulk testing, a swab may not be included in the receptacle 301, or if it is included may not be used. For example, a pill or other bulk substance may be inserted directly into the receptacle 301 for bulk testing.

Examples of the substances capable of detection include explosives, drugs, contaminated water, etc. At step 1401, the user removes the receptacle 301 from its protective packaging and removes the swab 330 from the receptacle 301. At step 1402, the user 202 decides whether trace or bulk collection is desired. If bulk collection is desired (step 1402=yes), for example, pill, rock of crack, etc. the user 202 need not replace the swab 330 and can place the bulk substance directly into the receptacle 301 at step 1405. If trace collection is desired (step 1402=no), the user takes the swab 330 and wipes the pad onto the trace substance, or otherwise applies the trace substance onto the pad without contaminating the pad 331 by contacting the pad 331 with a foreign surface. At step 1404, the user replaces the swab 330 into the receptacle 301 with the pad 331 containing the trace substance.

For the bulk and trace collection, the user 202 ruptures the ampoules 340 by applying pressure onto optional ribs 306 or 307 of receptacle 301. When the ampoules 340 are ruptured, reagent in the ampoules 340 travels out of the ampoules 340 downwardly through the tapered bottom walls 324 and the tapered lateral walls of the cavities 321 and into the testing area 319. At this point, at step 1407, a reaction occurs between the reagents and a substance on the pad 331, in which, depending upon the substance detected on the pad 331, turns the pad a particular color. At step 1408, the user uses the camera of the computing device 201 to capture an image of the pad 331, which is converted to a digital image in a known manner at step 1409. At step 1410, the colorimetric test is performed on the digital image. After the colorimetric test is complete, the result is displayed on the computing device 201. The result, can be transmitted via email, text, etc. and may include images of the scene and or suspect, test location on a map with or without GPS coordinates, notes, voice memo, and driver's license information. Additionally, the result can be transmitted with the manufacturing date and lot number of the receptacle 301, or any other information that may be useful to law enforcement or to courts.

In one embodiment, once the bulk substance or swab is inserted into the receptacle 301 for testing, the user seals the receptacle 301 with a pre-positioned adhesive on an opening flap of the receptacle 301. The user manually ruptures the one or more ampoules in the receptacle 301 and shakes the pouch to disperse the reagents within the pouch, down toward a bottom of the receptacle 301. The reagents react with the chemical on the pad of the swab or the bulk chemical, which can be observed by the user through the testing area. With the computing device 201, the user opens the application and uses the camera to focus on the substance to be tested and capture the substance being tested through the testing area, after aligning the identification code 311 on the receptacle 301 with alignment indicia generated by the application and displayed to the user 202 on the communication device 201. The application analyzes the colorimetric reaction and displays the result on the computing device 201.

FIGS. 15A and 15B show exemplary aligning indicia displayed on the computing device by the application with indicia such as an identification code 311 or other indicia on the pouch, according to an aspect of the present disclosure. With respect to FIG. 15A, after the swab 330 with the sample to be tested or bulk sample is inserted in to the receptacle 301, the user opens the application on the computing device 201 and activates the test by clicking a suitable icon on the display. The application then activates the user camera on the computing device 201. In one embodiment, the application automatically activates the camera, while in another embodiment, the user 202 opens the camera application manually. The display on the computing device 201 includes what the camera is viewing as the user 202 directs the camera at the pouch 301. The application will display a box, icon, image, or other indicia on the display of the computing device 201, which the user will use to align with an icon, image, or other indicia on the pouch 301. When the two are aligned, the application will read the icon, image or other indicia on the pouch and begin the test. In one embodiment, the test is begun automatically at this point. In another embodiment, once the alignment is achieved, the user will select an indicator on the screen or activate the camera shutter. In one embodiment, the application will provide an audio and/or visual indicator when alignment is achieved. The size of the identification code 311 is measured at a distance that the identification code 311 is from the computing device 201 when the identification code 311 is scanned by the application on the computing device 201. Based on the size of the identification code 311 when read by the application on the computing device 201, the application determines how big the testing window 310 is below the identification code 311 and adjusts to focus on just the testing window 310. Additionally, if the computing device 201 is positioned too far away or too close from the receptacle 301 during or prior to image capture (based on the size of the identification code 311), the application will alert the user (e.g., a visual or audible alert) to move the computing device 201 closer to or farther from the receptacle 301 to achieve the correct distance between the two. That is, monitoring and maintaining a consistent distance from the camera will ensure that a consistent number of pixels are captured from one test to another test by controlling the size of the test area, thus maximizing granularity and achieving detection at lower levels, resulting in reliable testing. In one aspect, a subsequent alert is provided to the user when the application determines that the receptacle 301 is at an acceptable distance from the computing device 201. In addition, when the identification code 311 is parallel with the computing device 201, dots or other markings (e.g., shown as three squares in the upper left, upper right, and lower left of the identification code 311 in FIG. 3) within the identification code 311 are equidistant from one another in the x-axis and y-axis directions. However, when the identification code 311 is not parallel with the computing device 201, then the dots or other markings in the identification code 311 lack this equidistant relationship when viewed from the perspective of the computing device 201. When a lack of a parallel relationship of the identification code 311 to the computing device 201 is detected during or prior to image capture, then the application will alert the user (e.g., visual or audible alert) to adjust the orientation of the receptacle 301 with respect to the computing device 201. In one aspect, a subsequent alert is provided to the user when the application determines that the identification code 311 is parallel to the computing device 201. That is, achieving the parallel relationship between the identification code 311 and the computing device 201 will ensure that a suitable image of the pad 331 is properly captured and that each part of the image is the same distance from the computing device, resulting in uniform images from test to test. In an alternative embodiment, with respect to FIG. 15B, the application on the computing device 201 displays a box on the display of the computing device which the user 202 aligns with a dot 371 on the receptacle 301. Instead of a dot, a square or other suitable indicia may be employed.

Figure 16:
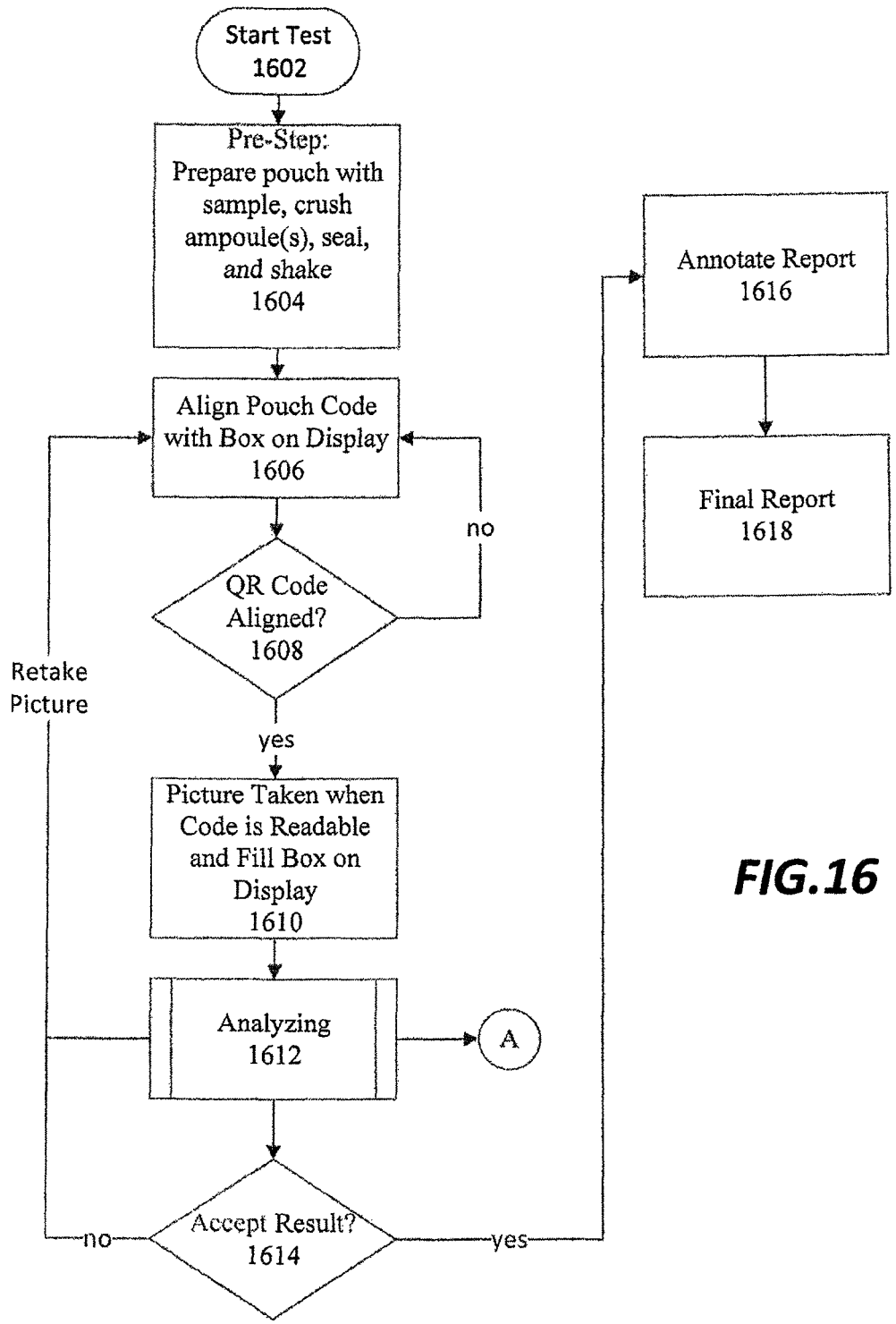
FIG. 16 shows an exemplary flow of the test process, according to an aspect of the present disclosure.

FIG. 16 show exemplary flows of the process of the method and system and the test process, according to an aspect of the present disclosure. While not shown, the system may include self-diagnostic test to determine the status of the application and/or imaging elements of the computing device. In embodiments, the application is implemented as software processes that are specified as a set of instructions recorded on a computer readable storage medium. When these instructions are executed by one or more computational or processing unit(s) (e.g., one or more processors, cores of processors, or other processing units), they cause the processing unit(s) to perform the actions indicated in the instructions. Examples of computer readable media include, but are not limited to, CD-ROMs, flash drives, random access memory (RAM) chips, hard drives, erasable programmable read-only memories (EPROMs), electrically erasable programmable read-only memories (EEPROMs), etc. The term software is intended to include firmware residing in read-only memory or applications stored in magnetic storage which can be read into memory for processing by a processor. In some embodiments, multiple software programs can be implemented as sub-parts of a larger program or programs while remaining distinct software programs. In some embodiments, multiple software programs can also be implemented as separate programs. Finally, any combination of separate programs that together implement a software program described herein is within the scope of the disclosure. In some embodiments, the software programs, when installed to operate on one or more electronic systems, define one or more specific machine implementations that execute and perform the operations of the software programs.

At step 1602, the user initiates the test on the computing device 201. At step 1604, the user places the bulk sample or swab 330 containing an amount of the sample into the receptacle 301 and seals the receptacle 301. The user 202 than manually ruptures the ampoule(s) 340 by squeezing the receptacle 301 at a position corresponding to the location of the ampoule(s) 340. In one embodiment, the pouch includes at least one marking indicating for the user 202 to locate where to squeeze and thus break the ampoule(s) 340. For example, at the ribs 306, 307 as shown in FIG. 4 or the markings 472 as shown in FIG. 11A. At step 1606, the user 202 aligns the identification code 311 on the receptacle 301 with indicia (e.g., a box) on the display of the computing device 201 displayed by the application. In one embodiment, the indicia on the screen may be a box configured to correspond with identification code 311 on the receptacle 301. At step 1608, the application determines whether the identification code 311 on the receptacle 301 is aligned with the indicia on the display of the computing device 201. If the identification code 311 on the receptacle 301 is not aligned with the indicia on the screen (step 1608=no), then processing waits for the user 202 to orient the computing device 201 so that alignment is achieved. When the identification code 311 is determined by the application to be aligned with the indicia on the display (step 1608=yes), a picture of the testing area is taken. At step 1610, the picture may be taken automatically upon alignment of the identification code 311, or the user 202 may activate the camera shutter or application icon. In one embodiment, an audio and/or visual indicator may be given to indicate identification code 311 alignment or a lack thereof.

At step 1612, the picture is analyzed in accordance with colorimetric software. If the application determines that the sample cannot be read, an audio and/or visual indication is provided to the user 202 to retake the picture of the sample. When the application determines that the picture is readable, colorimetric testing is performed and a result is displayed. In one embodiment, the colorimetric testing includes reading the color of the sample and comparing the color against known color standards, e.g., where the wavelength of the color of the sample is compared with known wavelengths. Thus, the testing identifies the sample by an analysis of a spectral pattern of the image of the sample. In one embodiment, the application may use a table, database, or other data structure for comparison with known color standards. The user 202 then has the option to redo the test by performing alignment and taking another picture or accepting the result at step 1614. If the result is accepted by the user 202, a final report is issued. At step 1616, the user then has the option to add various information to the report including, location information, scene information, suspect information, time/date information, etc. GPS or location information may be automatically added by the application receiving GPS coordinates from a GPS receiver of the computing device. A final report is generated at step 1618.

Figure 17A:
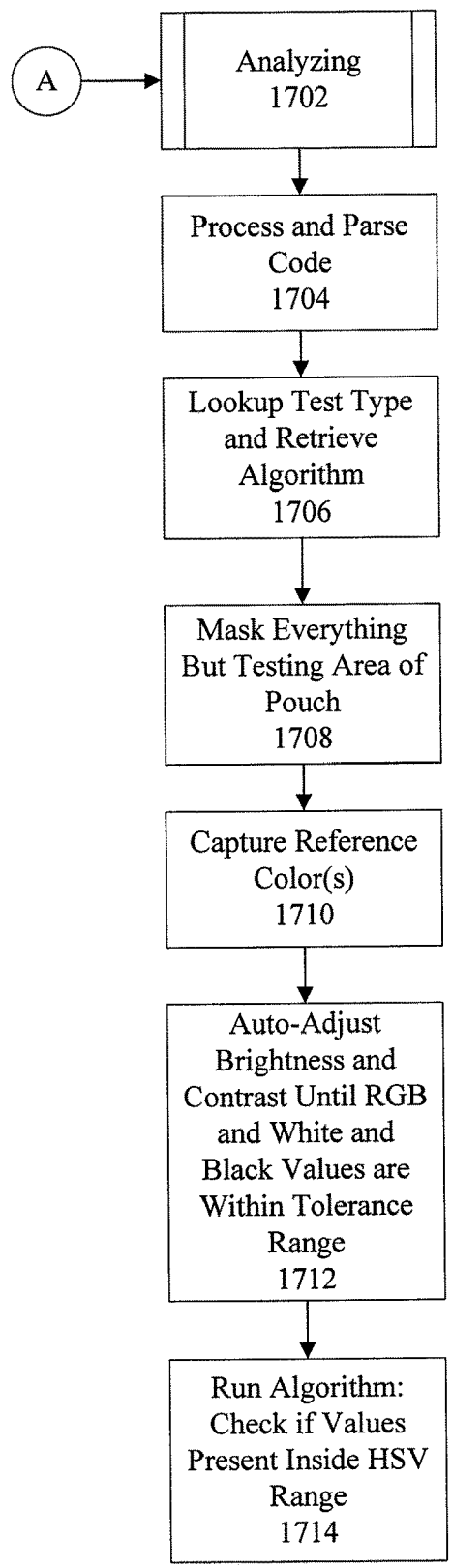
FIG. 17A shows an exemplary flow of a step in the test process shown in FIG. 16, according to an aspect of the present disclosure.

FIG. 17A show exemplary flows of the analysis of step 1612 of the method and system and the test process, according to an aspect of the present disclosure. In step 1702, the test application begins analyzing the sample. At step 1704, the identification code 311 is processed and parsed to identify the specific type of testing being conducted. At step 1706, the information parsed from the identification code 311 is used to determine the test type and obtain the algorithm corresponding to the test type. This information may be retrieved from a database with which the application on the computing device communicates.

At step 1708, the application masks out extraneous matter to exclude everything except that which appears in the testing area of the pouch. In step 1710, reference colors are captured, for example, from one or more swatches adjacent the testing area, for calibration purposes. At step 1712, the application auto-adjusts brightness and contrast until red green blue (RGB), white, and black values are within a predetermined tolerance range.

The application uses a white sample near or in lieu of the swatch 325 to perform color balancing and accurate color calibration of the captured image of the test area 319 by the computing device 201, including the pad 331 with the substance being tested, the reagent, and at least one of the swatch 325 and a white sample near or in lieu of the swatch 325. In an embodiment, the swatch 325 includes gray, red, green, blue, white, gray and/or other colors of the spectrum. If the swatch 325 includes a white sample, then a separate white sample is not necessarily employed.

For example, when an image of the test area 319 is captured by the computing device 201, which includes the pad 331 with the substance being tested, the reagent(s), and the swatch 325 or white sample, RGB algorithms are performed to take an offset from the captured colors to known colors. That is, the color data captured is transformed from acquired RGB values to new RGB values that are true colors.

In this regard, the application adjusts for various ambient lighting conditions present when the image is captured to in order to achieve RGB values that would exist under normal and ideal lighting conditions. For example, unfavorable lighting may exist on the test area 319 of the receptacle 301, which would affect how the application interprets the color of the reaction between the substance being tested and the reagent(s). As one example, the correction ensures that a purple dot is truly represented in the image as a purple dot, even if a yellow shadow is casted over it during image capture.

That is, the application uses the at least one color of the swatch 325 or the white sample, indicative of true color, to adjust the image colors.

For example, if an image of the test area 319 is captured that contains a white swatch on the receptacle 301, then the color of the swatch 325 in the image is compared to known ideal white RGB values. The offset can be taken for red, green, and blue RGB values for the white swatch color. This offset can be used over the remainder of the pixels in the image in order to balance the color in the entire image. Assuming that the offset is consistent over the entire image, the offset is effectively eliminated throughout the image.

In another embodiment, the red, green, and blue channels can all be used separately to take offsets of the given captured color swatch 325. These offsets can be used to balance the histogram of the entire image and accurately negate color casts and/or imbalances.

By implementing the RGB color adjustment algorithms, correct representation of consistent color can be achieved across different lighting scenarios.

At step 1714, the algorithm is run, and a check is performed as to whether values are presented within the color measurement schema, e.g., correct HSV color range.

The application is configured to detect specific wavelengths of colors detected from the image of the reaction on the pad 331 captured by the computing device 201 in order to achieve an objective and sensitive measure of the color obtained by the reaction between the substance being tested and the reagents.

In one embodiment, the optical system of the computing device can read the initial color corresponding to the spectral pattern of the substance on the test area of the pad for color bias correction. During the test, the spectral pattern is observed and recorded. The spectral pattern may correspond to targeted substances such as toxic chemicals, drugs, explosives, biological agents, and/or radioactive materials in the visible spectrum or in the invisible spectrum. The optical analysis is able to perform analysis over a broad spectrum including ultraviolet and infrared regions of the spectrum. In this embodiment the color pattern may be associated with a spectral pattern in a database and the unknown trace material is identified.

Figure 17B:
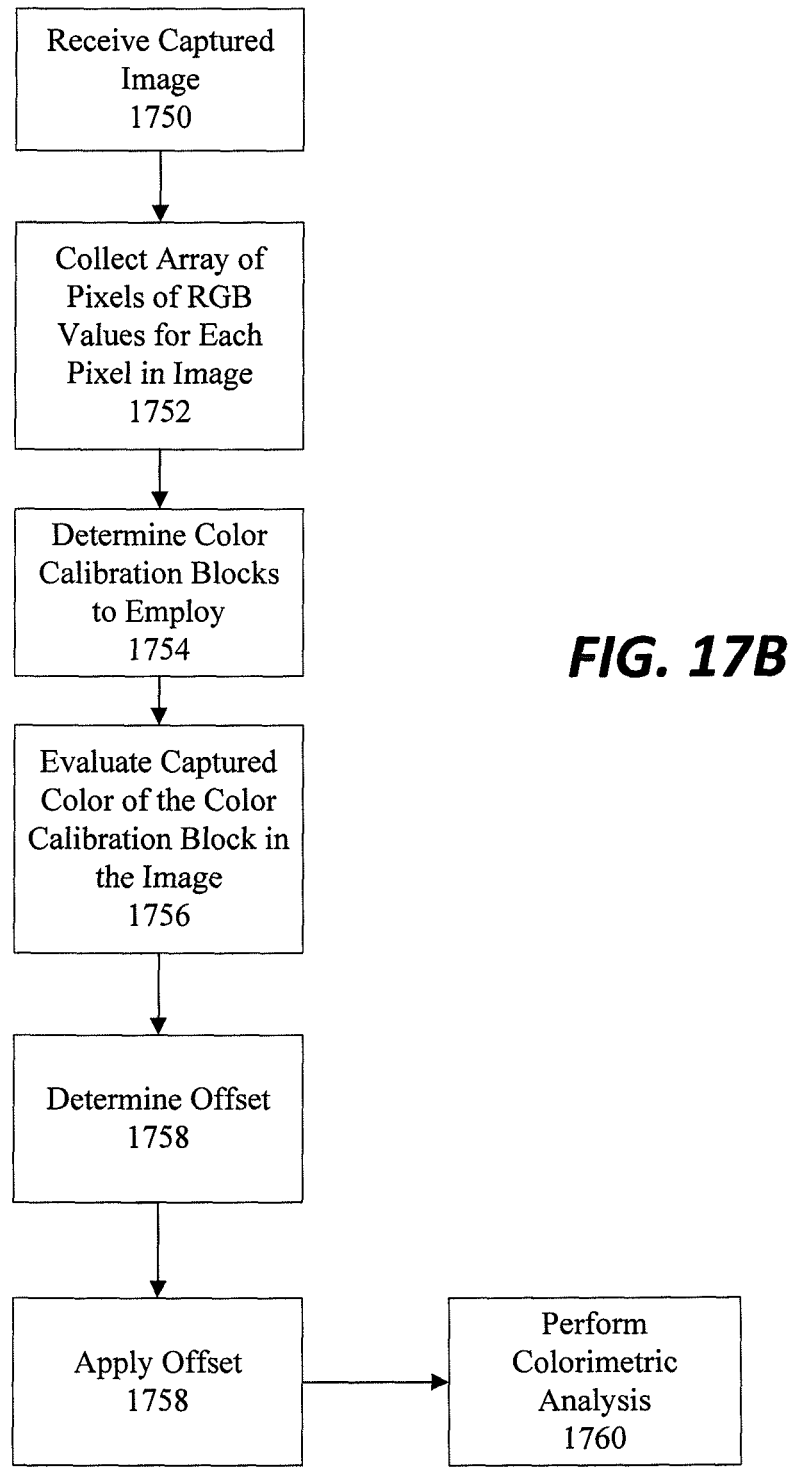
FIG. 17B show an exemplary flow for color balancing, according to an aspect of the present disclosure.

FIG. 17B show an exemplary flow for color balancing, according to an aspect of the present disclosure. At step 1750, an image is received of the reaction between the substance being tested and the reagent or reagents. The image includes the identification code 311 and the at least one color calibration swatch 325, also referred to as a color calibration sample block 325. That is, the color calibration swatch 325 may include a red, green blue block and/or a white, gray, black block. While the color calibration swatch 325 may include blocks various shapes, rectangular blocks provide uniform edges.

At step 1752, an array of pixels of RGB values for each pixel in the captured image is collected. At step 1754, a determination is made of which block in the color calibration swatch 325 to use in the evaluation is made. That is, the red, green, blue block and/or the white, gray, black block of the color calibration swatch 325 may be used. In one embodiment, the determination of which or whether both of the red, green, blue block and/or the white, gray, black blocks of the color calibration swatch 325 will be used in the evaluation of the captured image is made based upon the lighting conditions that existed when the image was captured. For example, in low light conditions such as night, both of the red, green, blue block and the white, gray, black blocks of the color calibration swatch 325 will be used. On the other hand, in daytime conditions with good lighting, only of the red, green, blue block and the white, gray, black blocks of the color calibration swatch 325 may be used. The determination of which color calibration swatch 325 to use in this aspect is thus based upon the time at which the image was captured, using for example, the time of the computing device 201 which is recorded at the time of image capture. In one embodiment, the user may indicate via selection of an appropriate selection on the application interface, for example, which of the red, green, blue block and/or the white, gray, black blocks of the color calibration swatch 325 will be used in the evaluation.

In lighting conditions affected by emergency vehicle lighting, both of the red, green, blue block and the white, gray, black blocks of the color calibration swatch 325 may be used. In another embodiment, the user may select whether the red, green, blue block and/or the white, gray, black blocks of the color calibration swatch 325 will be used in the evaluation. In this regard, the user may indicate which block to use at the time the image was captured, via an appropriate selection on the application interface, for example, a check box on the user interface to indicate that emergency vehicle lighting was present. Optionally, the user may enter the place and/or time in which the image was captured. Alternatively, the place that the image was captured may be obtained via GPS coordinates or other Geotags that are transmitted to the computing device 201 at the time the image was captured. For example, if it is determined by the application that the image was taken in a police facility according to the GPS coordinates or Geotags, then the application may assume that ideal lighting conditions existed at the time of image capture, such that only the white, gray, black blocks of the color calibration swatch 325 are used in the evaluation. Alternatively, if it is determined by the application that the image was taken in an outdoor setting according to the GPS coordinates or Geotags, then the application may assume that less than ideal lighting conditions may have existed at the time of image capture, such that both the red, green, blue blocks and the white, gray, black blocks of the color calibration swatch 325 are used in the evaluation. In another embodiment, the separate receptacles 301 may be used for good and poor light conditions, which may be identified by the application via reading the identification code 311 when capturing the image, and determining which or whether both of the red, green, blue block and/or the white, gray, black blocks of the color calibration swatch 325 will be used in the evaluation of the captured image.

In one embodiment, the application on the computing device 201 may, via a push or pull operation, obtain weather information from, for example, the Internet, such that the weather conditions at the time the image was captured may determine which of the red, green, blue block and/or the white, gray, black blocks of the color calibration swatch 325 will be used in the evaluation of the captured image. For example, in bright sunny days at the time of image capture, only the white, gray, black blocks of the color calibration swatch 325 may be used in the evaluation of the captured image. Whereas, in foggy and/or rainy conditions at the time of image capture, both of the red, green, blue block and/or the white, gray, black blocks of the color calibration swatch 325 may be used in the evaluation of the captured image. In this regard, the weather information may be used in conjunction with the location information as discussed above to determine whether the image capture was performed outdoors or indoors.

At step 1756, an evaluation of the captured color of the color calibration block in the image is performed. That is, an evaluation of whether the captured red from the red, green, blue block of the color calibration swatch 325 is true red is made. For example, during low light conditions or situations of light pollution, the captured red from the red, green, blue block of the color calibration swatch 325 may not appear as true red. The process is repeated for the captured green from the red, green, blue block of the color calibration swatch 325. The process is also repeated for the captured blue from the red, green, blue block of the color calibration swatch 325. If any of the captured red, green, or blue colors from the color calibration swatch 325 are not true red, green, or blue, than an offset of each color is determined.

Alternatively, or in addition to evaluating the captured red, green, and blue from the red, green, blue block of the color calibration swatch 325, the white from the white, gray, black block of the color calibration swatch 325 is evaluated to determine if the white is true white. The process is repeated for the captured gray from the white, gray, black block of the color calibration swatch 325. The process is repeated for the captured black from the white, gray, black block of the color calibration swatch 325. If any of the captured white, gray, or black colors from the color calibration swatch 325 are not true red, green, or blue, then an offset of each color is determined.

For example, a pixel of RGB color has red, green, and blue values therein. The image of the reagent and the targeted substance is captured and the red calibration color on the swatch 325 is determined to have a value of 225. According to an aspect of the present disclosure, the algorithm compares the value of 225 to ideal red which has a value of 255, and it determines that the offset is 30. Then, this offset of 30 is applied to every pixel in the captured image, such that every pixel in the image gets 30 added to the red channel in the RGB color. The other colors in the image are handled similarly.

At step 1758, for any determined offset in step 1756, the offset is applied to each pixel in the captured image to achieve color balancing. Thus, the colors in the captured image is now baselined, so that the colorimetric analysis may be performed at step 1760.

Figure 18C:
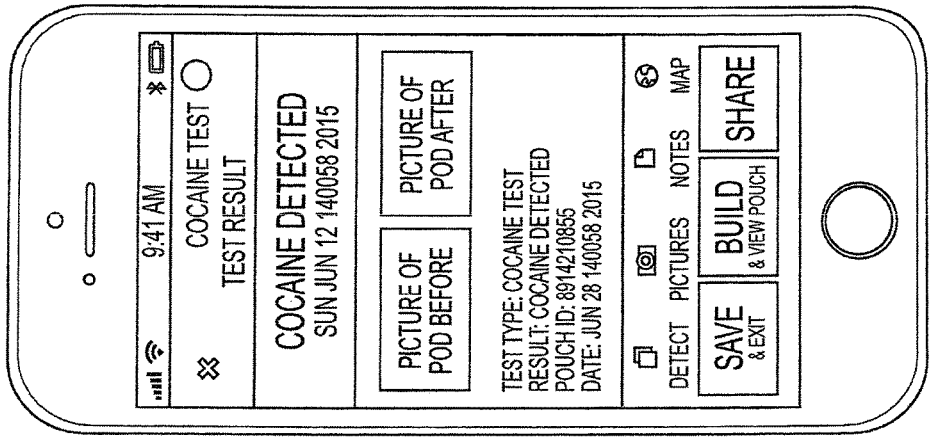
FIG. 18C is an exemplary screenshot, according to an aspect of the present disclosure.
Figure 18B:
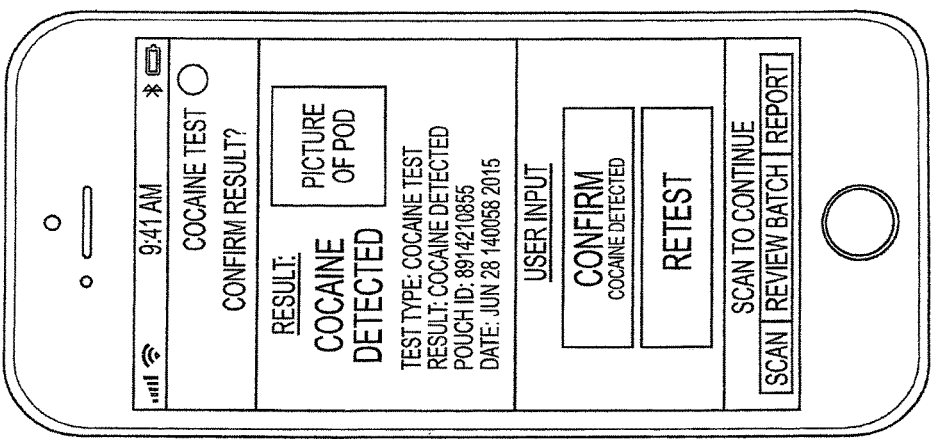
FIG. 18B is an exemplary screenshot, according to an aspect of the present disclosure.
Figure 18A:
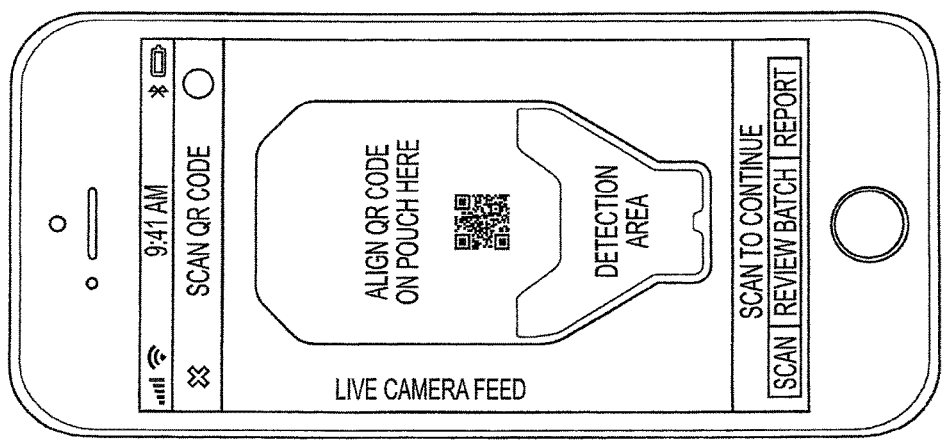
FIG. 18A is an exemplary screenshot, according to an aspect of the present disclosure.
Figures 19A, 19B, 19C:
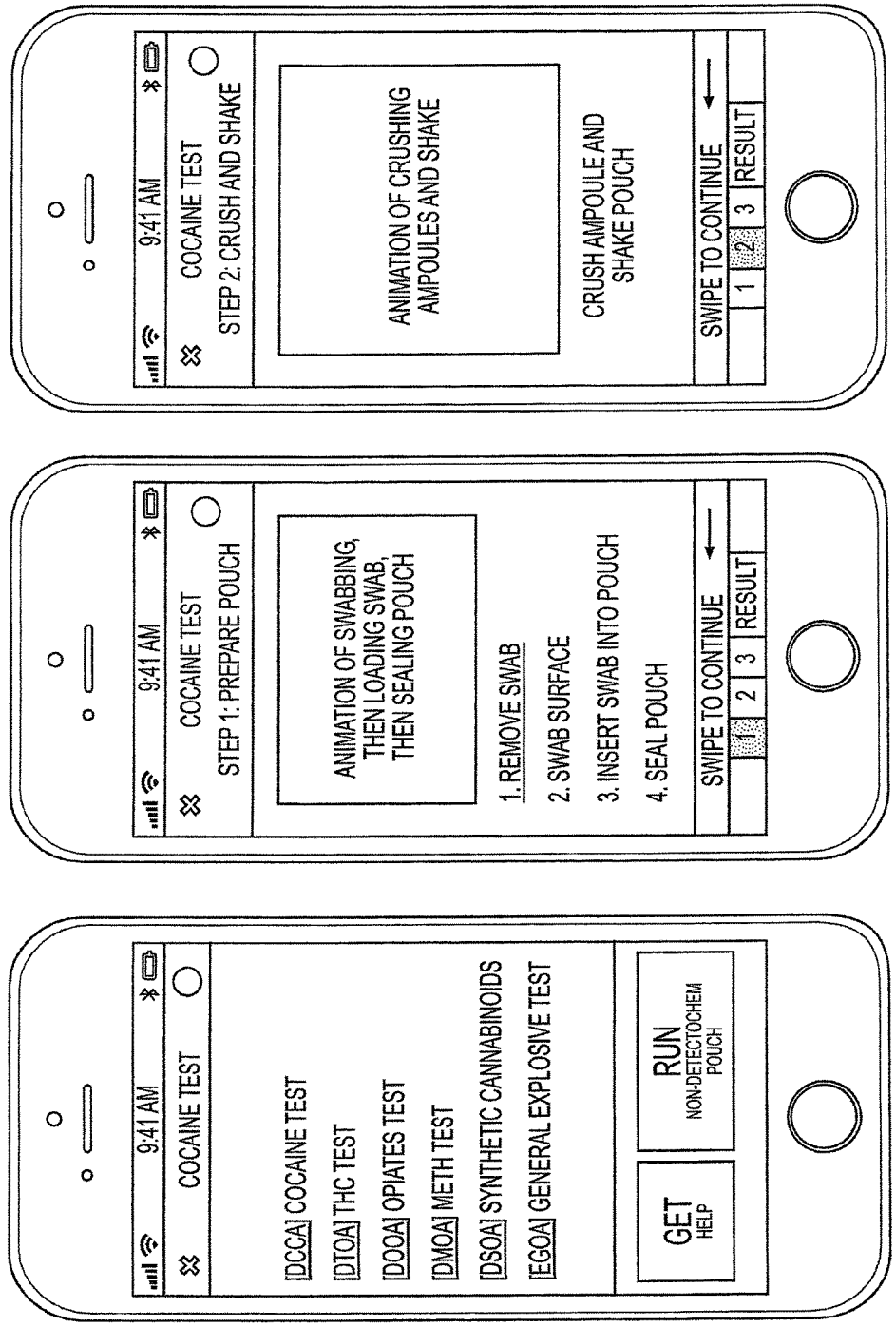
FIG. 19A is an exemplary screenshot, according to an aspect of the present disclosure.
FIG. 19B is an exemplary screenshot, according to an aspect of the present disclosure.
FIG. 19C is an exemplary screenshot, according to an aspect of the present disclosure.
Figures 19D, 19E, 19F:
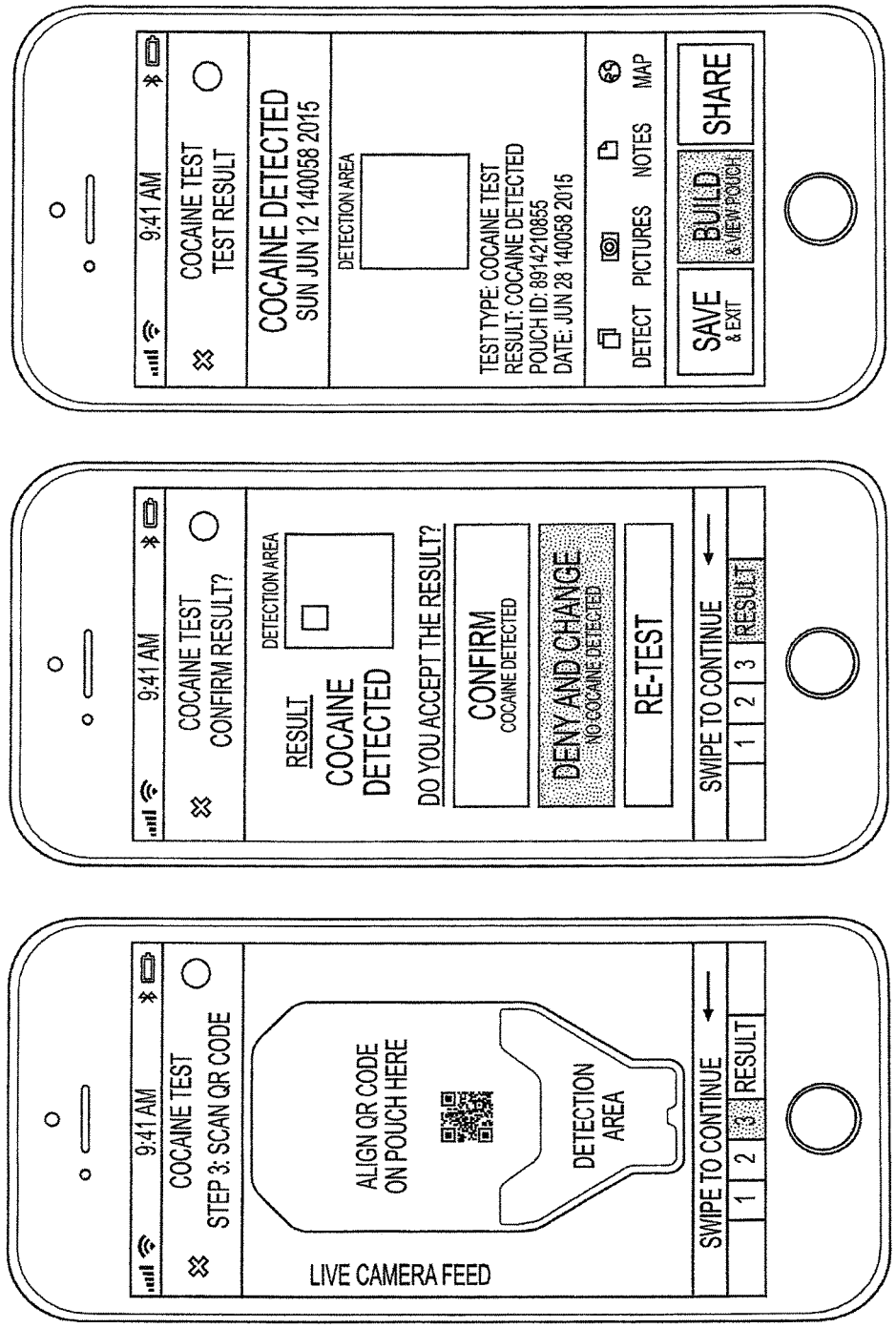
FIG. 19D is an exemplary screenshot, according to an aspect of the present disclosure.
FIG. 19E is an exemplary screenshot, according to an aspect of the present disclosure.
FIG. 19F is an exemplary screenshot, according to an aspect of the present disclosure.

FIGS. 18A, 18B, and 18C are exemplary screenshots according to an aspect of the present disclosure. The screen shot of FIG. 18A identifies to the user where to align the identification code 311 so that an image of the reaction may be captured. FIG. 18B indicates to the user that a positive cocaine result has been detected by the colorimetric test, and provides the user 202 with the opportunity to confirm the test or conduct a retest. FIG. 18C is a screenshot in a scenario in which the user 202 confirms the test.

FIGS. 19A, 19B, 19C, 19D, 19E, 19F are exemplary screenshots according to an aspect of the present disclosure. The screenshots of FIGS. 19A, 19B, 19C, 19D, 19E, 19F represent a tutorial configured to be optionally displayed to the user 202 that will guide the user 202 as to the operation of the application.

Figures 20A, 20B, 20C:
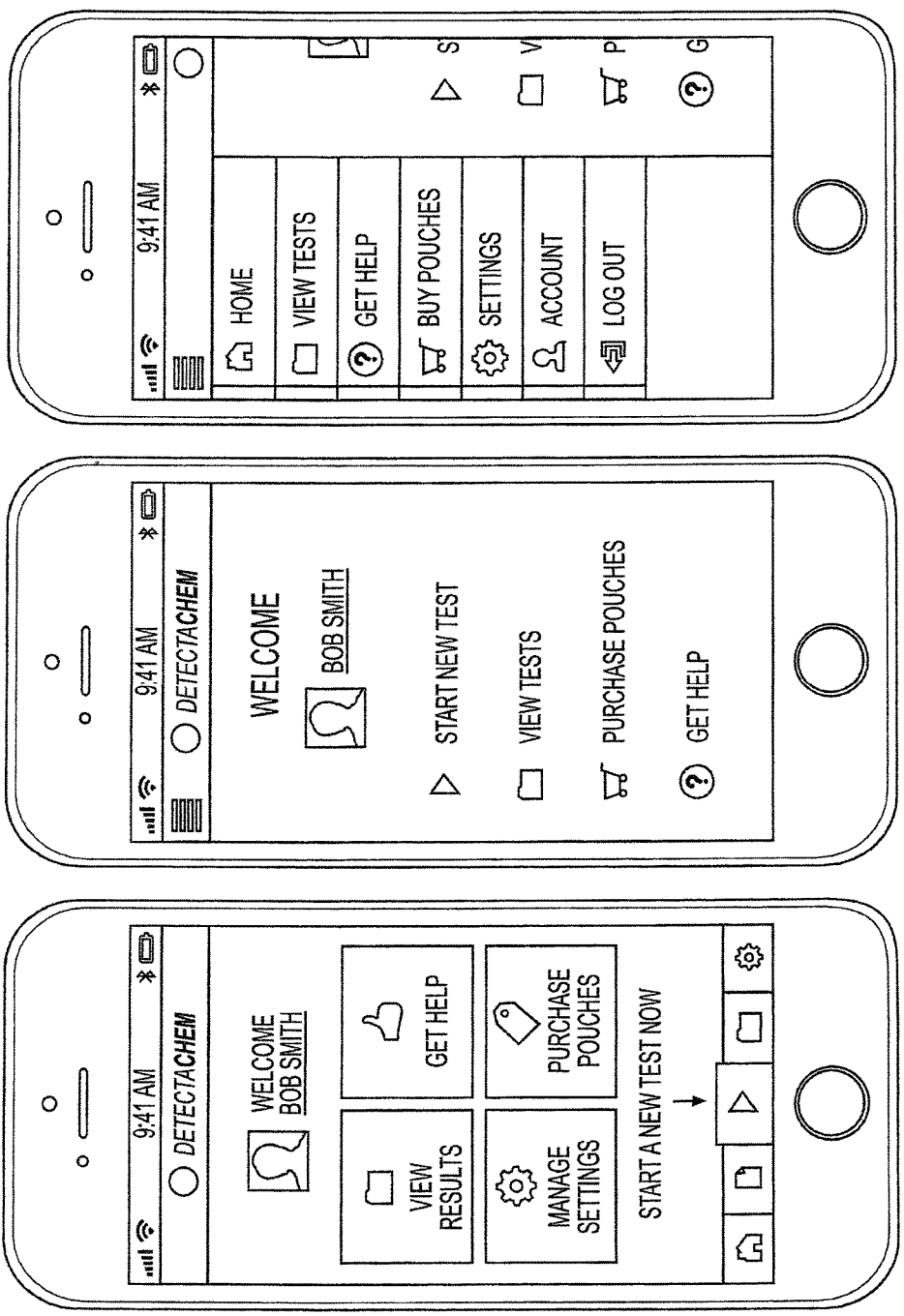
FIG. 20A is an exemplary screenshot, according to an aspect of the present disclosure.
FIG. 20B is an exemplary screenshot, according to an aspect of the present disclosure.
FIG. 20C is an exemplary screenshot, according to an aspect of the present disclosure.

FIGS. 20A, 20B, and 20C are exemplary screenshots according to an aspect of the present disclosure. FIGS. 20A, 20B, and 20C represent home screens that allows a user 202 to start a test, view test results, manage settings, purchase pouches, etc.

As discussed, a detection receptacle 301, computing device 201 such as a smartphone, operating system of the computing device 201, and detection application operate to perform targeted detection. In one embodiment, the application is a computer program designed to run on computing devices such as mobile devices, smart phones, tablet computers, laptops, notebooks, etc. The application may be pre-installed on the computing device 201 or downloadable from a supplier or application distribution platform. The application provides a user interface that allows users to align the pouch for testing, initiate the test, receive the test results, interpret the test results, store the test results, and/or transmit the test results over the network to which the computing device operates. When the test results are transmitted, the application may also include the GPS coordinates of the computing device, and other information relevant to law enforcement evidence collection and chain-of evidence protocols, such as date, time, name of suspect, driver's license information, etc.

In one embodiment, the pouches may include a plurality of swabs, allowing the user to select from one to perform the test. In this regard, the swabs may include different sizes, different shapes, or have different patterns. That is, certain swab configurations may be more adapted to test certain samples based upon, for example, the suspect nature of the sample to be tested. The pouch may include a clip or adhesive to provide for the secure closure thereof in order that the substance to be tested does not leak or does not become contaminated.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 182 that includes instructions 184 or receives and executes instructions 184 responsive to a propagated signal; so that a device connected to a network 101 can communicate voice, video or data over the network 101. Further, the instructions 184 may be transmitted or received over the network 101 via the network interface device 140.

Although the apparatus and method for the detection of trace and bulk substances has been described with reference to several exemplary embodiments, it is understood that the words that have been used are words of description and illustration, rather than words of limitation. Changes may be made within the purview of the appended claims, as presently stated and as amended, without departing from the scope and spirit of apparatus and method for the detection of trace substances in its aspects. Although apparatus and method for the detection of trace substances has been described with reference to particular means, materials and embodiments, apparatus and method for the detection of trace substances is not intended to be limited to the particulars disclosed; rather apparatus and method for the detection of trace substances extends to all functionally equivalent structures, methods, and uses such as are within the scope of the appended claims.

For example, the present disclosure contemplates the detection of illegal and legal substances such as chemicals (e.g., benzidines, aromatic amines, dioxins, furans, PCBs, pesticides, hydrocarbons, inorganic substances, metals, nitrosamines, ethers, alcohols, organophosphates, carbamates, halogenated pesticides, phenols, phenoxy acids, phthalates, radionuclides, volatile organic compounds), drugs (e.g., cannabis, cocaine, ecstasy, hallucinogens, heroin, methamphetamine, lysergic acid diethylamide (LSD), mushrooms, phencyclidine (PCP), inhalants, crack cocaine, ketamine, amphetamines, narcotics, barbiturates, steroids, opioids, synthetic drugs, hormones, depressants, antidepressants, fentanyl, suboxone), explosives (e.g., low explosives, high explosives, nitroglycerin, trinitrotoluene (TNT), C-4, PE-4, octogen (HMX), pentaerythritol tetranitrate (PETN), ammonium nitrate (ANFO), HMEs, triacetone triperoxide (TATP), hexamethylene triperoxide diamine (HMTD), nitrocellulose), and biological agents (e.g., bacterium, virus, protozoan, parasites, fungus, toxins, molds).

In one scenario, law enforcement can employ the disclosed apparatus and method to test substances in connection with arrests, police stops, searches, investigations, etc. Military personnel can employ the disclosed apparatus and method to test substances in connection with detection of explosives, biologic agents, chemical agents, etc. Parents can employ the disclosed apparatus and method to test for substances associated with their children. Parole or Probation officers can employ the disclosed apparatus and method to test for substances associated persons with whom they are responsible. In addition to hospital and medical personnel that can test substances associated with patients, administrators or officers of institutions such as schools and correctional settings can test substances associated with persons in their care. As another example, persons in the agricultural industry can test substances in soil. Additionally, residents can test substances for the presence of lead in paint or water; test for asbestos in homes; test for mold in homes; and test for nitrate, iron, manganese, PH, volatile organic compounds, fecal coliform, and/or *E. coli* in water sources.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. Accordingly, the disclosure is considered to include any computer-readable medium or other equivalents and successor media, in which data or instructions may be stored.

Although the present specification describes components and functions that may be implemented in particular embodiments with reference to particular standards and protocols, the disclosure is not limited to such standards and protocols. For example, standards and techniques such as (QR Code™, NFC, iBeacon, clickable paper, SnapTag, augmented reality, GOOGLE™ Goggles, UPC, RFID, image recognition, MICROSOFT™ Tag, barcode, OCR, machine readable indicia) represent examples of the state of the art. Such standards are periodically superseded by more efficient equivalents having essentially the same functions. Accordingly, replacement standards and protocols having the same or similar functions are considered equivalents thereof.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

According to an aspect of the present disclosure, a receptacle is provided for detecting a targeted substance. The receptacle includes at least one chamber configured to accommodate a reagent and a test swab, a first opening provided at a first end of the receptacle, a testing area provided at a second end of the receptacle, and an image readable by an image sensor and positioned a predetermined distance from the testing area, the image configured to facilitate alignment of the image sensor with the testing area for a colorimetric analysis.

According to another aspect of the present disclosure the at least one chamber is a first chamber and in which the at least one chamber and a second chamber are in fluid communication with each other, and the testing area is provided in the second chamber.

According to another aspect of the present disclosure, the receptacle includes a main body defined by the at least one chamber, at least one guide track extending through the main body from the first opening to the testing area, and a cover that seals the main body, the testing area and the guide track within the receptacle.

According to another aspect of the present disclosure, the receptacle includes at least one support wall extending across the guide track and configured to prevent a flow of liquid from the at least one chamber toward the first opening.

According to another aspect of the present disclosure, the cover includes a stepped portion that defines a transition between the first chamber and the second chamber.

According to another aspect of the present disclosure, a height of the first chamber is taller than a height of the second chamber.

According to another aspect of the present disclosure, the guide track includes tapered walls that are configured to guide the test swab into the receptacle toward the testing area.

According to another aspect of the present disclosure, at least one air hole is defined on a cover of the receptacle to communicate with an interior of the receptacle.

According to another aspect of the present disclosure the receptacle further includes color calibration indicia provided adjacent to the testing area to facilitate calibration of a reaction color based on the detection of the targeted substance for the colorimetric analysis.

According to yet another aspect of the present disclosure a detection kit for detection of a targeted substance is provided including a container housing at least one ampoule, the at least one ampoule containing at least one chemical reagent, the container including at least one test area that is visible through an exterior surface of the container, a swab receivable in the at least one test area, and a code on the exterior surface of the container at a predetermined distance from the test area, the code being readable by an image sensor, the code providing identification information associated with a detection of the targeted substance and providing an alignment reference for the image sensor, in which when a detection operation is performed, the at least one ampoule is ruptured to initiate a flow of the at least one chemical reagent to the at least one test area to react with a sample of the targeted substance on the swab for a colorimetric analysis after the code has been captured by the image sensor.

According to another aspect of the present disclosure color calibration indicia is provided adjacent the at least one test area.

According to another aspect of the present disclosure the color calibration indicia includes at least one calibration sample provided adjacent the at least one test area.

According to another aspect of the present disclosure the color calibration indicia facilitates the calibration of a reaction color for the colorimetric analysis.

According to another aspect of the present disclosure the color calibration indicia includes at least one color sample.

According to another aspect of the present disclosure the swab includes an elongated grip and a pad for collecting the sample of the targeted substance, the pad being provided on at least one longitudinal end of the swab.

According to another aspect of the present disclosure the pad includes at least one groove configured to collect trace amounts of material.

According to another aspect of the present disclosure the pad includes at least one raised area configured to collect trace amounts of material.

According to another aspect of the present disclosure the swab is removably insertable into the container to facilitate collection of the sample of the targeted substance and to facilitate placement within the container for detection.

According to another aspect of the present disclosure the container includes mounting protrusion configured to prevent the swab from contacting a distal end wall of the at least one test area.

According to yet another aspect of the present disclosure, a tangible non-transitory computer readable storage medium is provided that stores a computer program. The computer program, when executed by a processor, causes a computer apparatus to perform a process including interpreting a code on a test container, the code being readable by an image sensor and identifying a type of colorimetric analysis to be performed on a captured image of a sample, retrieving an algorithm corresponding to the type of colorimetric analysis to be performed, based on the interpreting of the code, masking information to retain image data associated with only a test area of the container, capturing at least one reference color from color calibration indicia provided adjacent the test area, detecting wavelengths of color obtained by a reaction between a sample in the test area at least one reagent in the test area, and identifying the sample by an analysis of a spectral pattern of the image of the sample.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to make or use the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A receptacle for detecting a targeted substance, comprising:
   at least one chamber configured to accommodate a reagent and a test swab;
   a first opening provided at a first end of the receptacle;
   a testing area provided at a second end of the receptacle; and
   an image readable by an image sensor and positioned a predetermined distance from the testing area, the image configured to facilitate alignment of the image sensor with the testing area for a colorimetric analysis based on the predetermined distance between the image and the testing area.

2. The receptacle of claim 1, wherein
   the at least one chamber is a first chamber and wherein the at least one chamber and a second chamber are in fluid communication with each other, and
   wherein the testing area is provided in the second chamber.

3. The receptacle of claim 1, further comprising
   a main body defined by the at least one chamber, at least one guide track extending through the main body from the first opening to the testing area, and
   a cover that seals the main body, the testing area and the guide track within the receptacle.

4. The receptacle of claim 3, further comprising
   at least one support wall extending across the guide track and configured to prevent a flow of liquid from the at least one chamber toward the first opening.

5. The receptacle of claim 2, wherein
the cover includes a stepped portion that defines a transition between the first chamber and the second chamber.

6. The receptacle of claim 2, wherein
a height of the first chamber is taller than a height of the second chamber.

7. The receptacle of claim 2, wherein
the guide track includes tapered walls that are configured to guide the test swab into the receptacle toward the testing area.

8. The receptacle of claim 1, further comprising
at least one air hole defined on a cover of the receptacle to communicate with an interior of the receptacle.

9. The receptacle of claim 1, wherein
the receptacle further comprises color calibration indicia provided adjacent to the testing area to facilitate calibration of a reaction color based on the detection of the targeted substance for the colorimetric analysis.

10. The receptacle of claim 1, wherein the at least one chamber is tapered to direct the reagent to flow towards the testing area.

11. The receptacle of claim 1, wherein
the at least one chamber is at least two chambers,
the receptacle further comprising:
  a main body;
  a neck portion extending from the main body;
  a base extending across the main body and the neck portion from a lower side thereof and including the at least two chambers configured to house frangible ampoules; and
  a cover sealed to and extending along peripheral upper side edges of the base and the neck portion, wherein
  the base includes a bottom wall that extends between the at least two chambers in a longitudinal direction of the receptacle, and
  the bottom wall includes a support wall extending in a lateral direction orthogonal to the longitudinal direction of the receptacle and projecting upward towards the cover.

* * * * *